United States Patent
DeSalles et al.

(10) Patent No.: US 9,597,007 B2
(45) Date of Patent: Mar. 21, 2017

(54) METHODS FOR THE IDENTIFICATION AND TARGETING OF BRAIN REGIONS AND STRUCTURES AND TREATMENTS RELATED THERETO

(75) Inventors: Antonio Alfonso Ferreira DeSalles, Los Angeles, CA (US); Alejandro Covalin, Culver City, CA (US)

(73) Assignees: THE REGENTS OF THE UNIVERSITY OF CALIFORNIA, Oakland, CA (US); U.S. DEPARTMENT OF VETERANS AFFAIRS, Washington, DC (US)

( * ) Notice: Subject to any disclaimer, the term of this patent is extended or adjusted under 35 U.S.C. 154(b) by 1356 days.

(21) Appl. No.: 13/386,312

(22) PCT Filed: Jul. 21, 2010

(86) PCT No.: PCT/US2010/042809
§ 371 (c)(1),
(2), (4) Date: Apr. 27, 2012

(87) PCT Pub. No.: WO2011/011554
PCT Pub. Date: Jan. 27, 2011

(65) Prior Publication Data
US 2012/0226138 A1    Sep. 6, 2012

Related U.S. Application Data

(60) Provisional application No. 61/227,394, filed on Jul. 21, 2009.

(51) Int. Cl.
*A61B 5/00* (2006.01)
*A61B 5/055* (2006.01)
*A61B 8/08* (2006.01)

(52) U.S. Cl.
CPC ............ *A61B 5/055* (2013.01); *A61B 5/4047* (2013.01); *A61B 5/4052* (2013.01); *A61B 5/4893* (2013.01); *A61B 8/0808* (2013.01)

(58) Field of Classification Search
CPC ..... A61B 5/055; A61B 5/4047; A61B 5/4052; A61B 5/4893; A61B 8/0808
See application file for complete search history.

(56) References Cited

U.S. PATENT DOCUMENTS 6,614,226 B2 *  9/2003  Wedeen ................. A61B 5/055
                                                    324/307
7,630,530 B2 * 12/2009  McGraw ............... G06T 7/0012
                                                    382/128

(Continued)

FOREIGN PATENT DOCUMENTS

WO    WO 2007/002144 A2    1/2007

OTHER PUBLICATIONS

Hadjipavlou et al. "Determining anatomical connectivities between cortical and brainstem pain processing regions in humans: A diffusion tensor imaging study in healthy controls." Pain 123, pp. 169-178. 2006.*

(Continued)

*Primary Examiner* — Amanda Lauritzen Moher
(74) *Attorney, Agent, or Firm* — Vista IP Law Group LLP

(57) ABSTRACT

Disclosed herein are methods for identifying and targeting brain regions and brain structures. In one embodiment, a method of identifying a brain structure in a patient comprises imaging a brain region using Diffusion Tensor Imaging MRI to identify a nerve tract, following the nerve tract to a first brain structure, and identifying the first brain structure based on the location and orientation of the nerve tract.

3 Claims, 8 Drawing Sheets

(56) References Cited

U.S. PATENT DOCUMENTS

| | | | |
|---|---|---|---|
| 7,949,401 B2* | 5/2011 | Fowler | A61N 2/006 600/13 |
| 8,077,937 B2* | 12/2011 | Niogi | G06K 9/3233 382/128 |
| 8,538,536 B2* | 9/2013 | Rezai | A61B 5/16 600/378 |
| 2002/0116042 A1* | 8/2002 | Boling | A61N 1/0531 607/122 |
| 2003/0009207 A1* | 1/2003 | Paspa | A61N 1/0529 607/116 |
| 2003/0149450 A1* | 8/2003 | Mayberg | A61N 1/08 607/3 |
| 2005/0065574 A1* | 3/2005 | Rezai | A61N 1/18 607/45 |
| 2006/0100671 A1 | 5/2006 | Ridder et al. | |
| 2007/0092120 A1* | 4/2007 | Guo | G06T 7/0083 382/128 |
| 2007/0127794 A1* | 6/2007 | Niogi | G06K 9/3233 382/128 |
| 2008/0039895 A1* | 2/2008 | Fowler | A61N 1/36025 607/2 |
| 2008/0046012 A1 | 2/2008 | Covalin et al. | |
| 2008/0064947 A1 | 3/2008 | Heruth et al. | |
| 2008/0123923 A1 | 5/2008 | Gielen et al. | |
| 2008/0157764 A1 | 7/2008 | Kabasawa et al. | |
| 2009/0149898 A1 | 6/2009 | Hulvershorn et al. | |
| 2009/0246140 A1 | 10/2009 | Covalin et al. | |
| 2016/0067495 A1* | 3/2016 | Chaturvedi | A61N 1/36128 607/59 |
| 2016/0220821 A1* | 8/2016 | O'Connell | A61N 2/006 |

OTHER PUBLICATIONS

DaSilva et al. "A primer on diffusion tensor imaging of anatomical substructures." Neurosurg Focus 15(1). 2003.*

Lujan, Chaturvedi, McIntyre. "Tracking the mechanisms of deep brain stimulation for neuropsychiatric disorders." Frontiers in Bioscience. 13: 5892-5904. 2008.*

Melega, William P. et al. "Hypothalamic Deep Brain Stimulation Reduces Weight Gain in an Obesity-Animal Model." PLoS One 7.1 (2012): e30672. PMC. Web. Aug. 19, 2016.*

Sedrak, M. et al., "The role of modern imaging modalities on deep brain stimulation targeting for mental illness", Acta Neurochir Suppl., vol. 101, pp. 3-7 (2008).

Ashford, Michael L. et al., "Glucose-induced excitation of hypothalamic neurones is mediated by ATP-sensitive K+ channels", Pflugers Arch 415 1990 , 479-483.

Author Unknown, American Cancer Society, "Cancer Facts & Figures 2008." American Cancer Society (2008).

Author Unknown, "University of Cincinnati researchers seek improved targeting in Parkinson's surgery," University of Cincinnati: pp. 1 (Jan. 2009).

Bagnol, Didier, "G-protein-coupled receptors in hypothalamic circuits involved in metabolic diseases," Current Opinion in Drug Discovery & Development 7(5) 2004, 665-682.

Baker, et al., "Sexual Receptivity and Ovulation in the Cyclic Rate Involves Protein-Synthesis in the Ventromedial Hypothalamus (Vmh) and Medial Preoptic Area (Mpoa) During Late Diestrus-li," Anatomical Record, vol. 199, No. 3, p. A16 (1981).

Baskin, Denis G. et al., "Leptin Receptor Long-form Splice-variant Protein Expression in Neron Cell Bodies of the Brain and Co-localization with Neuropeptide Y mRNA in the Arcuate Nucleus", J. Histochem Cytochem 47 1999 , 353-362.

Bayer, Laurence et al., "Alteration of expression of the hypocretin (orexin) gene by 2-deoxyglucose in the rat lateral hypothalamic area", NeuroReport 11 2000 , 531-533.

Benabid, Alim L. et al., "Mechanisms of Deep Brain Stimulation," Movement Disorders 17(3) 2002, 73-74.

Bernardis, et al., "The dorsomedial hypothalamic nucleus revisited: 1998 update," Proceedings of Society for Experimental Biology and Medicine, vol. 218, No. 4, pp. 284-306 (1998).

Berthoud, Hans-Rudolf, "Multiple neural systems controlling food intake and body weight," Neuroscience and Biobehavioral Reviews 26 2002, 393-428.

Brito, Marcia N. et al., "Differential Activation of the Sympathetic Innervation of Adipose Tissues by Melanocortin Receptor Stimulation," Endocrinology 148(11) 2007, 5339-5347.

Broadwell, Richard et al., "Entry of Peroxidase into Neurons of the Central and Peripheral Nervous Systems from Extracerebral and Cerebral Blood", J Comp Neur 166(3) 1976 , 257-284.

Broberger, Christian et al., "The neuropeptide Y/agouti gene-related protein (AGRP) brain circuitry in normal, anorectic, and monosodium glutamate-treated mice", Proc Natl Acad Sci USA 95 1998 , 15043-15048.

Broberger, et al., "Subtypes Y1 and Y2 of the neuropeptide Y receptor are respectively expressed in pro-opiomelanocortin-and neuropeptide-Y containing neurons of the rat hypothalamic arcuate nucleus," Neuroendocrinology, vol. 66, No. 6, pp. 393-408 (1997).

Broberger, et al., "Hypothalamic and vagal neuropeptide circuitries regulating food intake," Physiology & Behavior, vol. 74, No. 4-5, pp. 669-682 (2001).

Burdakov, Denis et al., "Orexin Excites GABAergic Neurons of the Arcuate Nucleus by Activating the Sodium-Calcium Exchanger", J. Neuroscience 23(12) 2003 , 4951-4957.

Canteras, N.S. et al., "Organization of Projections From the Ventromedial Nucleus of the Hypothalamus: A Phaseolus vulgaris-Leucoagglutinin Study in the Rat," The Journal of Comparative Neurology 348 1994, 41-79.

Castaneda, Tamara R. et al., "Symposium: Ghrelin: Its Role in Energy Balance, Obesity and the Neuroendocrine Control of Energy Homeostasis: The Role of Spontaneous Locomotor Activity", J Nutr 135 2005 , 1314-1319.

Chemelli, Richard M. et al., "Narcolepsy in orexin Knockout Mice: Molecular Genetics of Sleep Regulation", Cell vol. 98 1999 , 437-451.

Covalin, Alejandro et al., "Deep Brain Stimulation for Obesity Control: Analyzing Stimulation Parameters to Modulate Energy Expenditure," Conference on Neural Engineering, Arlington, VA, Mar. 16-19, 2005.

Covalin-Sharfman, Alejandro, "Deep Brain Stimulation to Modulate Energy Expenditure and Neurotrophic Factors," A Dissertation, University of California, Los Angeles, 2006.

Cowley, Michael A. et al., "Integration of NPY, AGRP, and Melanocortin Signals in the Hypothalamic Paraventricular Nucleus: Evidence of a Cellular Basis for the Adipostat," Neuron 24 1999, 155-163.

Cowley, Michael A. et al., "Leptin activates anorexigenic POMC neurons through a neural network in the arcuate nucleus," Nature 411 2001, 480-484.

Cowley et al., "The distribution and mechanism of action of ghrelin in the CNS demonstrates a novel hypothalamic circuit regulating energy homeostasis," Neuron, vol. 37, No. 4, pp. 649-661 (2003).

Cummings, David E. et al., "Melanocortins and body weight: a tale of two receptors," Nature Genetics 26, 2000, 8-9.

De Lecea, L et al., "The hypocretins: Hypothalamus-specific peptides with neuroexcitatory activity", Proc Natl Acad Sci USA 95 1998 , 322-327.

Defalco, Jeff et al., "Virus-assisted Mapping of Neural Inputs to a Feeding Center in the Hypothalamus", Science 291 2001 , 2608-2613.

Desalles, et al., "Functional Neurosurgery in the MRI Environment." Minim Invasive Neurosurg. 47(5): 284-289 (Oct. 2004).

Desalles, et al., "Radiosurgery from the Brain to the Spine: 20 years experience," Acta Neurochir Suppl. 2008.101: 163-8 (2008).

Dunn-Meynell, Ambrose A. et al., "Low-affinity sulfonylurea binding sites reside on neuronal cell bodies in the brain", Brain Research 745 1997 , 1-9.

Elias, Carol F. et al., "Leptin Activates Hypothalamic CART Neurons Projecting to the Spinal Cord", Neuron vol. 21 1998 , 1375-1385.

Elias, Carol F. et al., "Leptin Differentially Regulates NPY and POMC Neurons Projecting to the Lateral Hypothalamic Area", Neuron 23 1999 , 775-786.

(56) References Cited

OTHER PUBLICATIONS

Elmquist, Joel K. et al., "Anatomic basis of leptin action in the hypothalamus," Neuroendocrinology of Leptin, vol. 26, pp. 21-41 (2000).

Elmquist, Joel K. et al., "Leptin activates distinct projections from the dorsomedial and ventromedial hypothalamic nuclei," Proc. Natl. Acad. Sci. USA 95 1998, 741-746.

Evans, William J. et al., "Cachexia: A new definition," Clinical Nutrition 27 2008, 793-799.

Fadel, et al., "Anatomical Substrates of Orexin-Dopamine Interactions: Lateral Hypothalamic Projections to the Ventral Tegmental Area," Neuroscience, vol. 111, No. 2, pp. 379-387; p. 379, col. 2, para 1, p. 385, col. 1 para 2. (2002).

Fan, et al., "Cholecystokinin-mediated suppression of feeding involves the brainstem melanocortin system." Nat. Neurosci. 7, 335-336 (2004).

Flanagan, Loretta M. et al., "Gastric motility in conscious rats given oxytocin and an oxytocin antagonist centrally," Brain Research 578 1992, 256-260.

Foster, Alan C. et al., "Melenocortin-4 Receptor Antagonists as Potential Therapeutics in the Treatment of Cachexia," Current Topics in Medicinal Chemistry 7 2007, 1131-1136.

Foster, et al., MC4 receptor antagonists: A potential treatment for cachexia, Idrugs, vol. 8, No. 4, pp. 314-319, (2005).

Fulwiler, Carl E. et al., "Cholecystokinin-Immunoreactive Innervation of the Ventromedial Hypothalamus in the Rat: Possible Substrate for Autonomic Regulation of Feeding", Neuroscience Letters 53 1985 , 289-296.

Guan et al., "Evidence of altered hypothalamic pro-piomelanocortin neuropeptide Y mRNA expression in tubby mice," Molecular Brain Research, vol. 59, No. 2, pp. 273-279 (1998).

Guan, et al., "Orexinergic innervation of POMC-containing neurons in the rat arcuate nucleus," Neuroreport, vol. 12, No. 3, pp. 547-551 (2001).

Hahn, Tina M. et al., "Coexpression of Agrp and NPY in fasting-activated hypothalamic neurons", nature neuroscience 1 (4) 1998 , 271-272.

Hakansson, M.-L. et al., "Leptin Receptor- and STAT3-Immunoreactivities in Hypocretin/Orexin Neurones of the Lateral Hypothalamus", J. Neuroendocrinology 11 1999 , 653-663.

Hamani, Clement, et al., "Memory Enhancement Induced by Hypothalamic/Fornix Deep Brain Stimulation," Annals of Neurology 63 (2008) 119-123.

Harnack, Daniel et al., "The effects of electrode material, charge density and stimulation duration on the safety of high-frequency stimulation of the subthalamic nucleus in rats," Journal of Neuroscience Methods 138 2004, 207-216.

Haynes, Andrea C. et al., "Effects of single and chronic intracerebroventricular administration of the orexins on feeding in the rat", Peptides 20 1999 , 1099-1105.

Hoge, et al., "Linear Coupling Between Cerebral Blood Flow and Oxygen Consumption in Activated Human Cortex," PNAS, vol. 96, pp. 9403-9408, abstract, p. 9407, col. 2, para 4 to p. 9408, col. 1, para 2 (1999).

Horvath, et al., "Synaptic interaction between hypocretin (Orexin) and neuropeptide Y cells in the rodent and primate hypothalamus: A novel circuit implicated in metabolic and endocrine regulations," Journal of Neuroscience, vol. 19, No. 3, pp. 1072-1087 (1999).

Hotz, Hubert G. et al., "An Improved Clinical Model of Orthotopic Pancreatic Cancer in Immunocompetent Lewis Rats," Pancreas 22(2) 2001, 113-121.

Inui, Akio, Cancer Anorexia-Cachexia Syndrome: Current Issues in Research and Management, A Cancer Journal for Clinicians 52 (2002) 72-91.

Iversen, "Canabis and the Brain," Brain, vol. 126, pp. 1252-1270; p. 1254, col. 2, para 1; pp. 1257, col. 2, para 3, p. 1260, col. 1, para 1, 3 (2003).

Jobst, Erin E. et al., "The electrophysiology of feeding circuits," Trends in Endocrinology and Metabolism 15(10) 2004, 488-499.

Joppa, M.A. et al., "Central infusion of the melanocortin receptor antagonist agouti-related peptide (AgRP(83-132)) prevents cachexia-related symptoms induced by radiation and colon-26 tumors in mice," Peptides 28 (2007) 636-642.

Kennedy, Adele et al., "The Metabolic Significance of Leptin in Humans: Gender-Based Differences in Relationship to Adiposity, Insulin Sensitivity, and Energy Expenditure," Journal of Clinical Endocrinology and Metabolism 82(4) (1997) 1293-1300.

Kopell, Brian H. et al., "Neuromodulation Surgery for Psychiatric Disorders", emedicine from WebMD http://emedicine.medscape.com/article/1343677-overview 2008 , 23 pages.

Kristensen, Peter et al., "Hypothalamic CART is a new anorectic peptide regulated by leptin", Nature 393 (1998) 72-76.

Kruk, Menno R. , "Ethology and Pharmacology of Hypothalamic Aggression in the Rat", NeuroScience & Biobehavioral Reviews 15 (1991), 527-538.

Lacan, Goran et al., "Modulation of food intake following deep brain stimulation of the ventromedial hypothalamus in the vervet monkey," J. Neurosurg. 108 (2008) 336-342.

Laviano, Alessandro et al., "Neural control of the anorexia-cachexia syndrome", Am J Physiol Endocrinol Metab 295 (2008) E1000-E1008.

Laviano, et al., "NPY and brain monoamines in the pathogenesis of cancer anorexia," Nutrition, vol. 24, No. 9, pp. 802-805 (2008).

Lin et al., "The sleep disorder canine narcolepsy is caused by a mutation in the hypocretin (orexin) receptor 2 gene," Cell, vol. 98, No. 3, pp. 365-376 (1999).

Lund, Per-Eric et al., "The Orexin OX1 Receptor Activates a Novel Ca2+ Influx Pathway Necessary for Coupling to Phospholipase C*", J. Biol Chem 275 (40) 2000 , 30806-30812.

MacDonald, Neil et al., "Understanding and Managing Cancer Cachexia," Palliative Care 197(1) (2003) 143-161.

Markison, Stacy et al., "The Regulation of Feeding and Metabolic Rate and the Prevention of Murine Cancer Cachexia with a Small-Molecule Melanocortin-4 Receptor Antagonist," Endocrinology 146(6) 2005, 2766-2773.

Marks, et al., "Differential role of melanocortin receptor subtypes in cachexia." Endocrinology 144, 1513-1523 (2003).

Matsuda, et al., "Altered Hypothalamic Function in Response to Glucose Ingestion in Obese Humans," Diabetes, vol. 48, pp. 1801-1806; Abstract, Fig. 1A-B; p. 1802, col. 1, para 1-2, p. 1802, col. 2, para. 3 (1999).

Mayberg Helen S. et al., "Deep Brain Stimulation for Treatment-Resistant Depression," Neuron 45 (2005) 651-660.

McIntyre, Cameron C., "Finite Element Analysis of the Current-Density and Electric Field Generated by Metal Microelectrodes," Annals of Biomedical Engineering 29 (2001) 227-235.

Mercer, et al., "Coexpression of leptin receptor and preproneuropeptide Y mRNA in arcuate nucleus of mouse hypothalamus," Journal of Neuroendocrinology, vol. 8, No. 10, pp. 733-735 (1996).

Morley, John E. et al., "Cachexia: pathophysiology and clinical relevance," The American Journal of Clinical Nutrition 83 (2006) 735-743.

Muroya, Shinji et al., "Glucose-sensitive neurons in the rat arcuate nucleus contain neuropeptide Y", Neuroscience Letters 264 (1999) 113-116.

Murphy, E.J., "Stable isotope methods for the in vivo measurement of lipogenesis and triglyceride metabolism." J Anim. Sci. 84 Suppl, E94-104 (2006).

Muscaritoli, Maurizio et al., "Prevention and treatment of cancer cachexia: New insights into an old problem," European Journal of Cancer 42 (2006) 31-41.

Narita, K et al., "Subthalamic locomotor region is involved in running activity originating in the rat ventromedial hypothalamus", Behav Brain Research 134 (2002) 275-281.

Nishimura, Hiroyuki et al., "Effects of Hypothalamic Stimulation on Activity of Dorsomedial Medulla Neurons That Respond to Subdiaphragmatic Vagal Stimulation", J Neurophysiology 58(4) 1987 , 655-675.

Peyron, Christelle et al., "Neurons Containing Hypocretin (Orexin) Project to Multiple Neuronal Systems", J Neuroscience 18(23) (1998) 9996-10015.

(56) References Cited

OTHER PUBLICATIONS

Plumb, J.A. et al., "Energy expenditure and protein synthesis rates in an animal model of cancer cachexia," Clinical Nutrition 10 (1991) 23-29.

Ruffin, Marie-Pierre et al., "Electrical stimulation of the ventromedial hypothalamus enhances both fat utilization and metabolic rate that precede and parallel the inhibition of feeding behavior," Brain Research 846 (1999) 23-29.

Sakurai, Takeshi et al., "Orexins and Orexin Receptors: A Family of Hypothalamic Neuropeptices and G Protein-Coupled Receptors that Regulate Feeding Behavior", Cell 92 (1998) 573-585.

Schubert, et al., "Cancer chemoprevention by the antioxidant tempol in Atm-deficient mice." Human Molecular Genetics 13, 1793-1802 (2004).

Schwartz, Michael W. et al., "Central nervous system control of food intake," Nature 404 (2000) 661-671.

Sedrak, M. et al., "The role of modern imagine modalities on deep brain stimulation targeting for mental illness," Acta Neurochir Suppl 101 (2008) 3-7.

Shannon, R.V., "A Model of Safe Levels for Electrical-Stimulation." IEEE Transactions on Biomedical Engineering 39, 424-426 (1992).

Shioda, Sheiji et al., "Immunohistochemical localization of leptin receptor in the rat brain", Neuroscience Letters 243 (1998) 41-44.

Shimazu, T., "Central Nervous System Regulation of Liver and Adipose Tissue Metabolism," Diabetologia 20 (1981) 343-356.

Shiraishi, Takemasa et al., "Effects of leptin and orexin-A on food intake and feeding related hypothalamic nerons", Physiology & Behavior 71 (2000) 251-261.

Sternson, Scott M. et al., "Topographic mapping of VMH → arcuate nucleus microcircuits and their reorganization by fasting," Nature Neuroscience 8(10) 2005, 1356-1363.

Suzuki, Ryusuke et al., "Orexin-1 receptor immunoreactivity in chemically identified target neurons in the rat hypothalamus", Neuroscience Letters 324 (2002) 5-8.

Takahashi, Akira et al., "Hypothalamic Regulation of Lipid Metabolism in the Rat: Effect of Hypothalamic Stimulation on Lipolysis," Journal of the Autonomic Nervous System 4 (1981) 195-205.

Tataranni, P.A., "Mechanisms of Weight Gain in Humans," European Review for Medical and Pharmacological Sciences, vol. 4, pp. 1-7, p. 5, col. 1, para 2, p. 5, col. 2, para 1 (2000).

Temel, et al., "Deep Brain Stimulation of the Thalamus Can Influence Penile Erection," International Journal of Impotence Research, vol. 16, pp. 91-94, p. 92, col. 2, para 4 to p. 93, col. 2, para 1 (2004).

Ter Horst, G., et al., "Phaseolus-Vulgaris Leuco-Agglutinin Tracing of Intrahypothalamic Connections of the Lateral, Ventromedial, Dorsomedial and Paraventricular Hypothalamic Nuclei in the Rat," Brain Research Bulletin, vol. 18, No. 2, pp. 191-203 (1987).

Thompson, R.H. et al., "Organization of inputs to the dorsomedial nucleus of the hypothalamus: a reexamination with Fluorogold and PHAL in the rat", Brain Research Reviews 27 (1998) 89-118.

Thornhill, J.A. et al., "Electrical stimulation of the posterior and ventromedial hypothalamic nuclei causes specific activation of shivering and nonshivering thermogenesis", Can J Physiol Pharmacol 72 (1994) 89-96.

Thornhill, J et al., "Intrascapular brown adipose tissue (IBAT) temperature and blood flow responses following ventromedial hypothalamic stimulation to sham and IBAT-denerverated rats", Brain Research 615 (1993) 289-294.

Tyler, William J. et al., "Remote Excitation of Neuronal Circuits Using Low-Intensity, Low-Frequency Ultrasound," PLoS One 3(10) 2008, 1-11.

Vissing, J. et al., "Ventromedial hypothalamic regulation of hormonal and metabolic responses to exercise," The American Journal of Physiology—Regulatory, Integrative and Comparative Physiology 256 (1989) 1019-1026.

Viswanadha, et al., "Optimized conditions for measuring lipolysis in murine primary adipocytes." J Lipid Res. 47, 1859-1864 (2006).

Wang, Jian et al., "Central insulin inhibits hypothalamic galanin and neuropeptide Y gene expression and peptide release in intact rats", Brain Research 777 (1997) 231-236.

Wikberg, Jarl E. et al., "Targeting melanocortin receptors: an approach to treat weight disorders and sexual dysfunction," Nature Reviews Drug Discovery (published online) 2008, 1-17.

Williams, Gareth et al., "The hypothalamus and the control of energy homeostasis, Different circuits, different purposes," Physiology & Behavior 74 (2001) 683-701.

Woods, Stephen C. , "Gastrointestinal Satiety Signals, I. An overview of gastrointestinal signals that influence food intake", Am J Physiol Gastrointest Liver Physiol 286 (2004) G7-G13.

Wynne, Katie et al., "Appetite control," Journal of Endocrinology 184 (2005) 291-318.

Yamada, Hiroto et al., "Inhibition of Food Intake by Central Injection of Anti-orexin Antibody in Fasted Rats", Biochemical and Biophysical Research Communications 267 (2000) 527-531.

Yee, et al., Magnetic Resonance Imaging, 20, pp. 17-26 (2002).

Zhang, Xeuguo et al., "Stimulation of the paraventricular nucleus modulates the activity of gut-sensitive neurons in the vagal complex", Am J. Physiol Gastrointest Liver Physiol 277 (1999) 79-90.

Zhao et al., "Comparison of TCA and ICA Techniques in fMRI Data Processing," Journal of Magnetic Resonance Imaging, vol. 19, pp. 397-402, abstract, p. 398, col. 1, para 5 to p. 398, col. 2, para 2, p. 401, col. 1, para 2 (2004).

\* cited by examiner

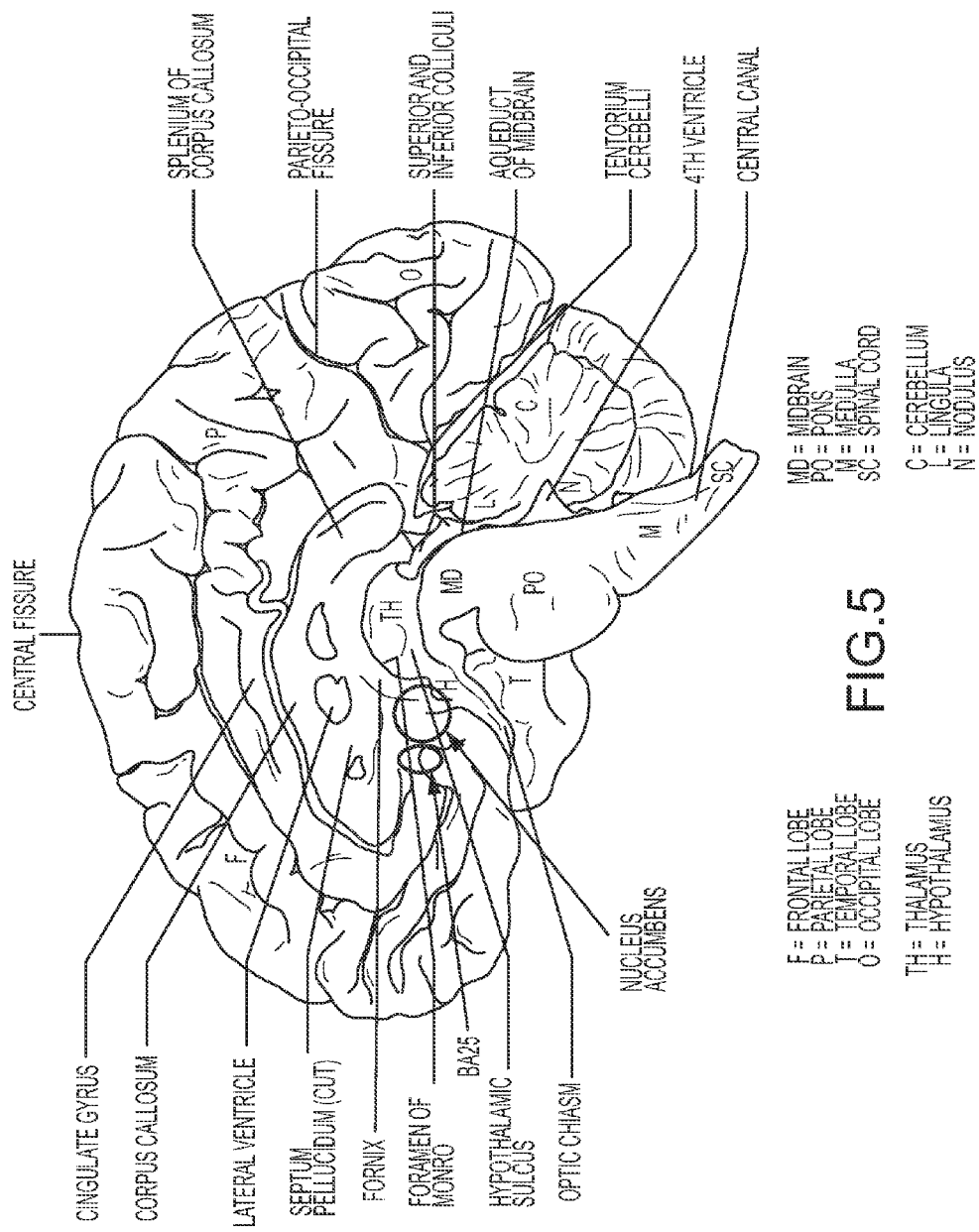

METHODS FOR THE IDENTIFICATION AND TARGETING OF BRAIN REGIONS AND STRUCTURES AND TREATMENTS RELATED THERETO

CROSS REFERENCE TO RELATED APPLICATIONS

This application is a U.S. National Stage filing under 35 U.S.C. §371 of International Application No. PCT/US2010/042809, filed Jul. 21, 2010, which also claims priority to U.S. Application No. 61/227,394, filed Jul. 21, 2009 and entitled "Methods For The Identification and Targeting of Brain Regions and Structures" which are incorporated by reference herein in its entirety. Priority to the aforementioned applications are hereby expressly claimed in accordance with 35 U.S.C. §§119, 120, 365 and 371 and any other applicable statutes.

This application is also related to U.S. patent application Ser. No. 12/411,710 which was filed Mar. 26, 2009, and is entitled "Methods for Identifying and Targeting Autonomic Brain Regions," which claims priority to U.S. Patent Application No. 61/039,671, which was filed Mar. 26, 2008, and is entitled "Methods for Identifying and Targeting Autonomic Brain Regions," both of which are incorporated by reference herein in their entirety.

STATEMENT REGARDING FEDERALLY SPONSORED RESEARCH OR DEVELOPMENT

This work was supported by the U.S. Department of Veterans Affairs, and the Federal Government has certain rights in the invention.

FIELD

The present disclosure relates generally to methods of identifying and targeting brain regions, such as hypothalamic brain regions, and brain structures by identifying afferent and/or efferent connections, such as nerve tracts or fiber tracts, related thereto.

BACKGROUND

One common technique to target brain regions, e.g., neural structures, that are part of the central nervous system (CNS) and are functionally connected with the autonomic nervous system (ANS) and that have no unique or clearly identified direct correlation with human senses (i.e., vision, hearing, touch, smell, and taste) is via anatomical references. These anatomical references are derived via population studies; the anatomical location in a particular patient may be identified using magnetic resonance imaging (MRI) and comparing the MRI anatomical image with the above-mentioned anatomical references derived via population studies.

In the only human case using deep-brain stimulation (DBS) targeting hypothalamic structures that are related to the energy homeostasis system, and specifically the ventromedial hypothalamic nucleus (VMH), the target (i.e., the VMH) location was estimated using a computed tomographic scan (CT scan) which is similar to an MRI. The scan provided anatomical information to be used as a reference. After the electrode was at the estimated target, the electrode position was confirmed by asking the patient if he felt less hunger (i.e. subjective data).

Provided herein are methods of identifying and targeting autonomic brain regions and treatments related thereto.

SUMMARY

Disclosed herein are methods of identifying a brain structure in a patient. In one aspect, the method comprises imaging a brain region using Diffusion Tensor Imaging MRI to identify a nerve tract, following the nerve tract to a first brain structure, and identifying the first brain structure based on the location and orientation of the nerve tract. The nerve tract can be selected from the group consisting of the fornix, the stria terminalis, the mammillothalamic tract, the dorsal longitudinal fasciculus, the anterior commissure, the optic tract, the ventral amygdalofugal pathway, the hypothalamic-hypophyseal tract, the dorsal longitudinal bundle, the medial forebrain bundle, the cingulate gyrus fibers, the ansa lenticularis, the lenticular fasciculus, the subthalamic-occipitoparietal fibers, frontal fibers traversing the internal capsule and the dentorubrothalamic fascicle. The first brain structure can be selected from the group consisting of the ventromedial hypothalamic nucleus, the perifornical region, the lateral hypothalamic area, the dorsomedial hypothalamic nucleus, the arcuate nucleus, the subgenual area (brodmann area 25), the subthalamic nucleus and the paraventricular nucleus.

In one aspect, the first brain structure is the dorsomedial portion of the ventromedial hypothalamic nucleus and the nerve tract is selected from the group consisting of the stria terminalis and the dorsal longitudinal fasciculus.

In other aspects, the first brain structure comprises the perifornical region and the nerve tract is selected from the group consisting of the fornix and the ventral amygdalofugal pathway.

In still other aspects, the first brain structure comprises the lateral hypothalamic area and the nerve tract is selected from the group consisting of the fornix, the ventral amygdalofugal pathway, the dorsal longitudinal bundle and the medial forebrain bundle.

In still other aspects, the first brain structure comprises the paraventricular nucleus and the nerve tract is the hypothalamic-hypophyseal tract.

In still other aspects, the first brain structure comprises the subgenual area and the nerve tract is the Cingulate Gyrus fibers.

In still other aspects, the first brain structure comprises the subthalamic nucleus and the nerve tract is selected from the group consisting of the ansa lenticularis, the lenticular fasciculus, the subthalamic-occipitoparietal fibers, frontal fibers traversing the internal capsule and the dentorubrothalamic fascicle.

In some aspects, the method further comprises modulating the activity of the first brain region or the nerve tracts related to the first brain region by electrical deep brain stimulation, local drug delivery, ultrasound, transcranial magnetic stimulation, or energy beams.

Disclosed herein is a kit comprising a deep brain stimulation device and instructions for performing the method of identifying a brain structure in a patient as disclosed herein.

BRIEF DESCRIPTION OF THE DRAWINGS

FIG. 5 depicts a sagittal view of several brain regions wherein the brodmann area and the nucleus accumbens is shown.

DETAILED DESCRIPTION

Figure 1:
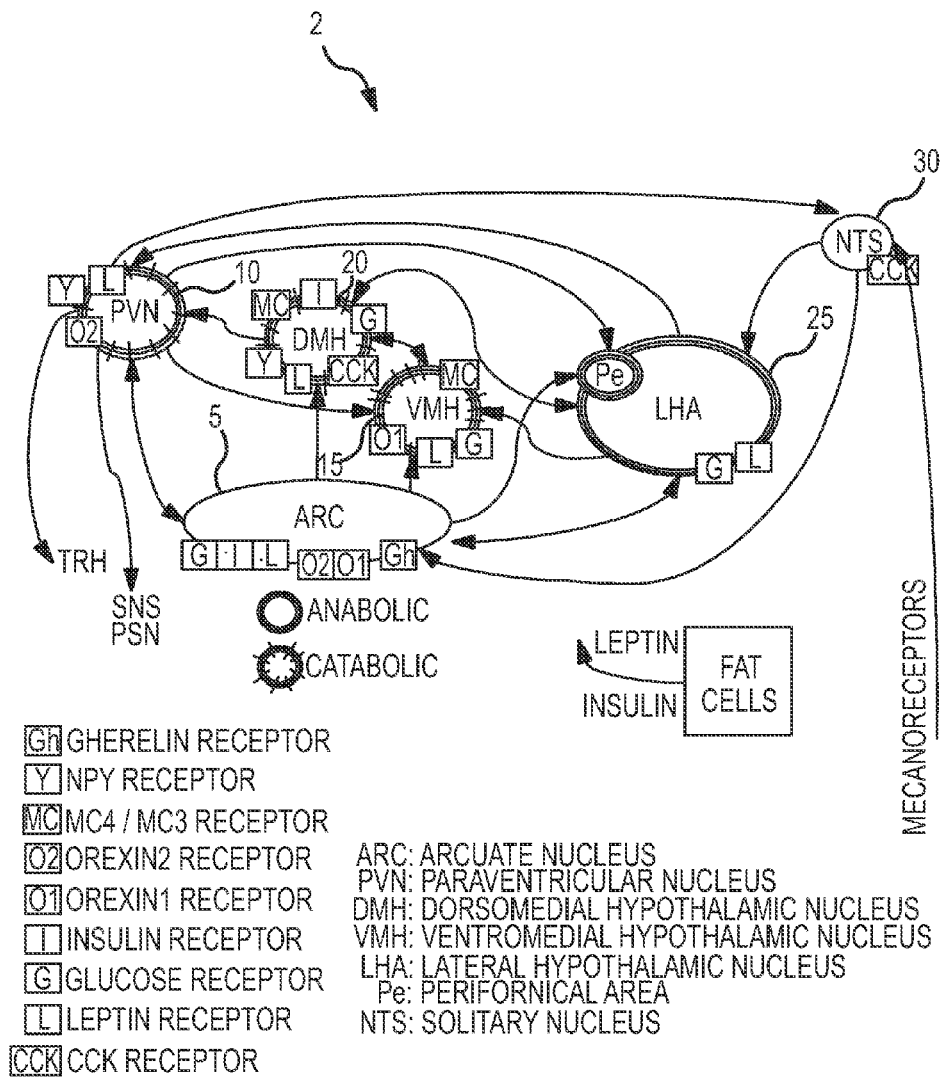
FIG. 1 depicts brain structures within the hypothalamic brain region.

The present disclosure provides methods of identifying brain structures of a brain region, such as the hypothalamic brain region, by identifying afferent and/or efferent connections, such as nerve tracts or fiber tracts, related thereto. The present disclosure also provides methods of treating diseases and conditions by modulating the activity of the brain structure or the nerve tracts related thereto which may be identified by the methods disclosed herein. The present disclosure also provides kits comprising a deep brain stimulation device and instructions for performing the method of identifying a brain structure in a patient as disclosed herein.

In certain embodiments, the disclosure provides methods of identifying deep brain regions that are the target in deep-brain stimulation (DBS). In some embodiments, the deep brain regions are hypothalamic regions, including hypothalamic structures involved in the energy homeostasis system. These structures or brain nuclei may include subsets of the VMH, such as the dorsomedial portion of the VMH and the ventrolateral portion of the VMH, functional portions of the ventromedial hypothalamic nucleus (VMH), the perifornical region (Pe), the lateral hypothalamic area (LHA), the dorsomedial hypothalamic nucleus (DMH), the arcuate nucleus (ARC), and the paraventricular nucleus (PVN). In some embodiments, the method disclosed herein may be used to identify the subgenual area (brodmann area 25) and/or the nucleus accumbens. In other embodiments, the method disclosed herein may be used to identify the subthalamic nucleus (STN).

The regions or the structures may be imaged during an MRI by a technique known as Diffusion Tensor Imaging (DTI), and a particular brain structure can be identified by its afferent or efferent connections with other brain structures, by reference to other brain structures or by their proximity to other brain structures. That is, for example, by imaging the hypothalamus using DTI MRI, nerve tracts can be identified and followed and used as landmarks or pathways to help identify the target brain region or brain structure.

After identifying the brain structure(s) by following the nerve tract(s) to the brain structure(s) and selecting a reference, the exact position of the brain structure/target area is coded into three-dimensional (3D) coordinates. The information obtained from the DTI MRI can also be used to plan the trajectory or angle of implantation of the electrode such that surrounding tracts and vasculature may be avoided. These 3D coordinates are used to implant an electrode or a cannula to deliver a therapy to the brain structure or to collect information. For example, an electrode may be used to activate or inhibit neural activity by passing current into the brain structure or an electrode may be used to record neural activity. An electrode may also be used to activate or inhibit neural activity by passing current into a nerve tract directly or indirectly related to the brain structure in order to modulate neural activity of a particular brain structure. The cannula may be used for delivering a therapeutic agent or collecting samples. The electrode(s) may also be mounted onto or into the cannula.

Because the afferent and efferent connections are functional links, these connections may be used to identify brain structures without having to rely solely upon a comparison to general anatomical reference points that may vary across a given population. An ordinarily skilled artisan will recognize that instead of using data obtained in a population study, the methods described herein may rely on data obtained before the surgery from each individual patient to identify the desired neural region(s) or structure(s). The methods disclosed herein may also confirm the placement of the electrode during the surgical procedure (intra-operatively) using both objective measurements (e.g., EE, VCO2, VO2, the absence of tremors in a patient with a movement disorder such as Parkinson's Disease, and other measurements) and subjective measurements (e.g., ask the patient to report on unpleasant sensations such as dizziness or a change in mood).

I. Afferent and Efferent Connections

In the nervous system, there is a "closed loop" system of decision, reactions and sensation. These decision-making processes are carried out via the interaction of neural networks that may be distributed across different brain structures (i.e., nuclei). Information may be carried into each brain structure via its afferent connections and may be sent out of the brain structure via its efferent connections. As used herein, the terms "afferent" and "efferent" are used to describe relative connections between nervous structures, such as brain regions, brain structures, or brain nuclei. The term "afferent" means to conduct inward, for example, a particular afferent nerve tract conducts information into a brain area (e.g. a brain region or a brain structure). The term "efferent" means to conduct outward, for example, a particular efferent nerve tract conducts information out of a brain area (e.g. a brain region or a brain structure). As used herein, the terms "nerve tracts" and "fiber tracts" may be used interchangeably and may be used to refer to the efferent and afferent connections, individually or collectively.

Disclosed herein are methods of identifying a brain structure by its afferent/efferent connections (e.g. the nerve tracts leading to and from a brain structure), by the afferent/efferent connections that connect a first brain structure with a second brain structure, by reference to afferent/efferent connections between other brain structures or by the brain structure's proximity to afferent/efferent connections between other brain structures. The afferent/efferent connections between brain regions, such as between the hypothalamus and the amygdala, may also be used to identify brain structures within a brain region.

Because the afferent/efferent connections can be functional links, using them to identify brain structures may reduce the inaccuracies associated with identification of a particular brain region by comparison to anatomic reference points established for an averaged population. The methods disclosed herein identify the connections between neural structures in order to identify particular brain structures based on reference to those functional connections on a patient by patient basis.

For example, by imaging autonomic brain regions, such as the hypothalamus, using DTI MRI, nerve tracts such as, but not limited to, the fornix, the stria terminalis, the mammillothalamic tract, the dorsal longitudinal fasciculus, the anterior commissure, the optic tract, the ventral amygdalofugal pathway, and the medial forebrain bundle can be identified and used as landmarks to identify a brain structure of interest.

Figure 2:
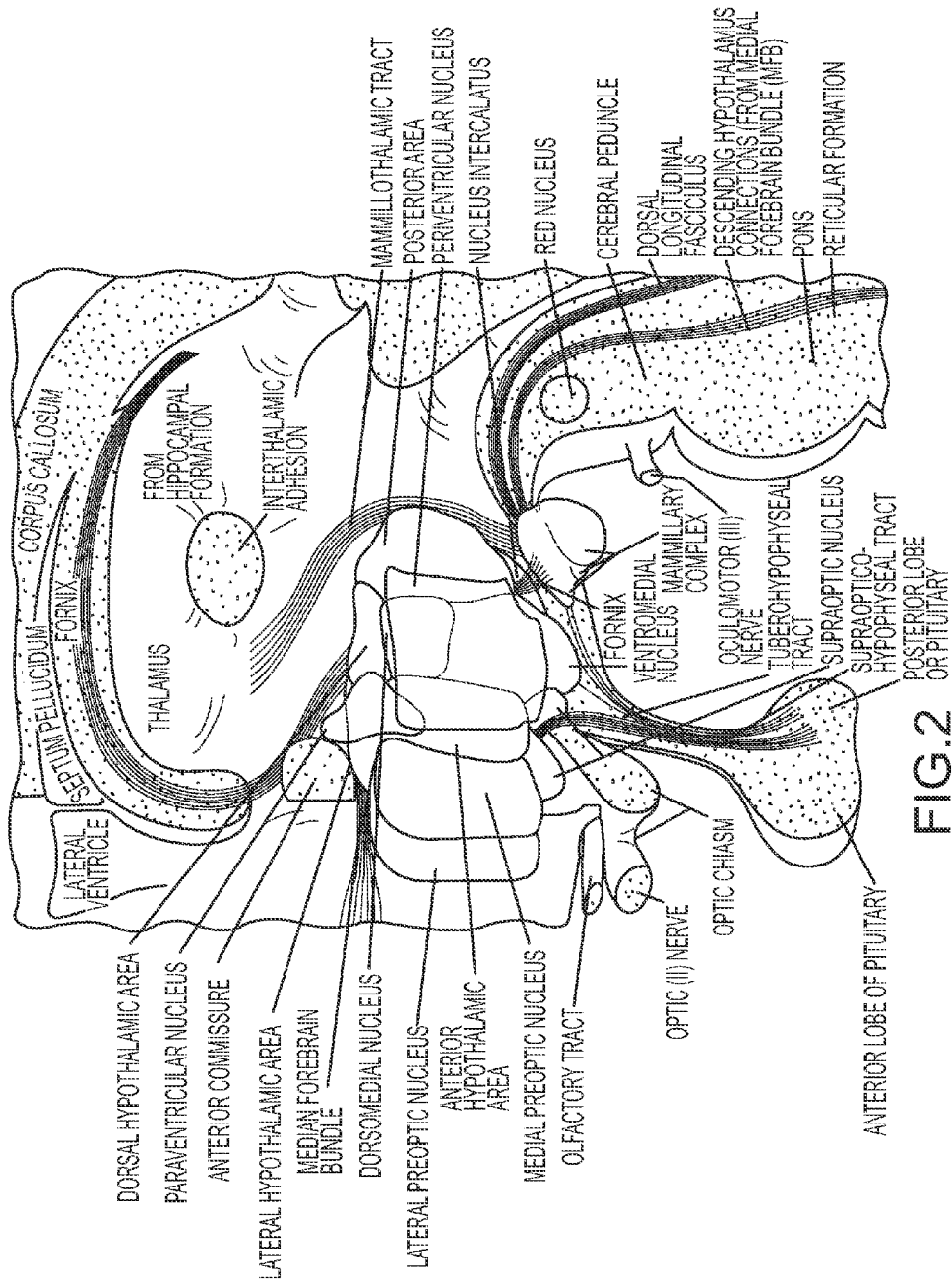
FIG. 2 depicts several brain regions, brain structures and nerve tracts found therein.
Figure 3:
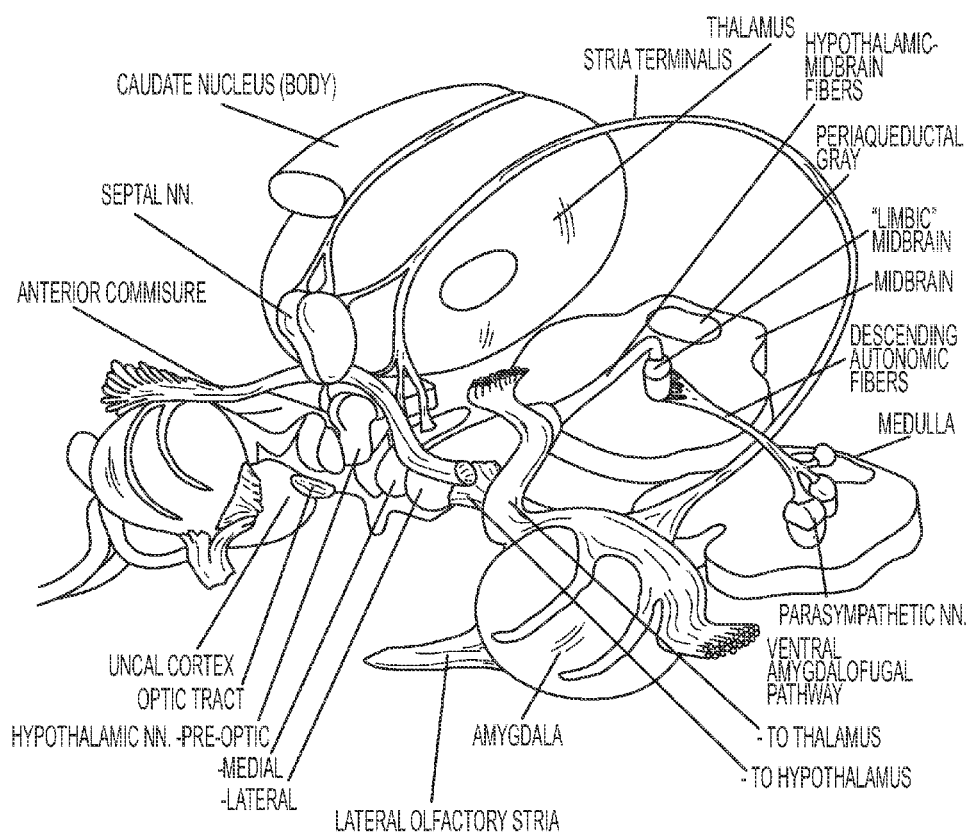
FIG. 3 depicts an additional view of the several brain regions, brain structures and nerve tracts found therein of FIG. 2.
Figure 4:
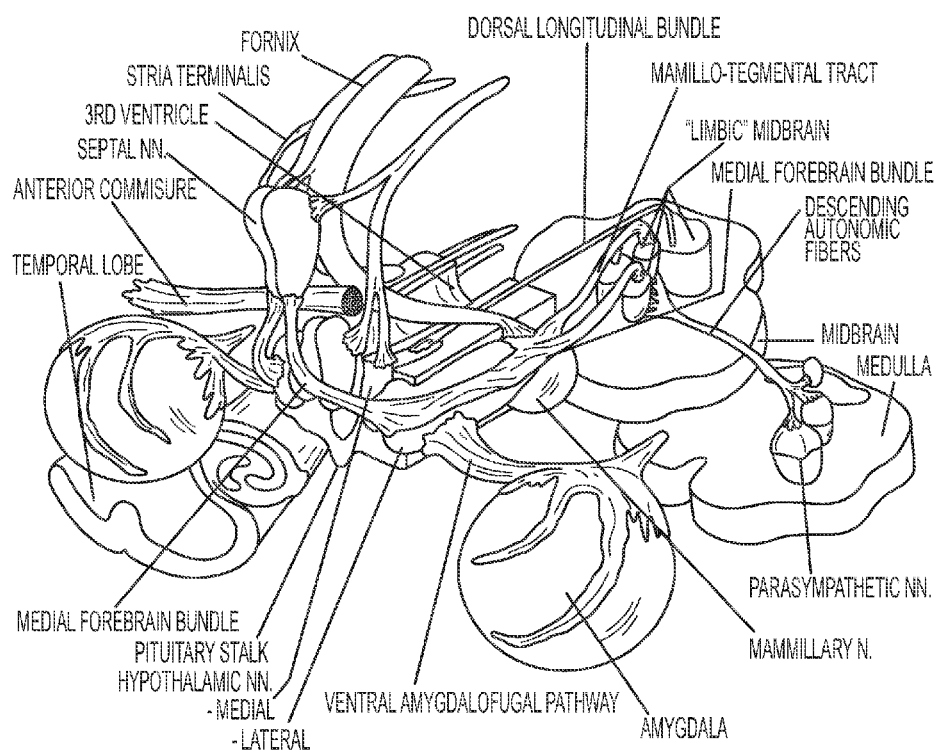
FIG. 4 depicts an additional view of the several brain regions, brain structures and nerve tracts found therein of FIG. 2.

In some embodiments, the nerve tracts are used to identify the desired hypothalamic or other brain region target by, for example, using DTI to follow the nerve tract into the target itself. For example, and as can be understood with reference to FIGS. 3 and 4 (which are reproduced from Walter J. Hendelman, Atlas of Functional Neuroanatomy, $2^{nd}$ ed. Published/distributed: Boca Raton, Fla.: CRC Taylor & Francis, 2006), the ventral amygdalofungal pathway goes into the lateral hypothalamic area (LHA). Thus, by identifying the ventral amygdalofungal pathway (e.g. by DTI) and then following the pathway (e.g. by DTI), the LHA can be identified. In some embodiments, the nerve tracts are used to identify a first brain structure relative to a second brain structure. That is, the nerve tracts leading to a second brain structure are followed to identify the location of the second structure. The location of the first brain structure is then identified with reference to the second brain structure. For example, as can be understood from FIGS. 1-3 (FIG. 2 is reproduced from Netterimages.com, Elsevier, Inc. Image 29435), the stria terminalis and the dorsal longitudinal fasciculus nerve tracts are recognized and their terminations identified by DTI. A branch of the stria terminalis carries fibers from the VMH to the amygdala located dorsally from the VMH and arching around the thalamus. The dorsal longitudinal fasciculus originates in the hypothalamic nuclei located medially around the third ventricle and then travels posteriorly before turning ventrally. The location of the dmVMH may be determined by identifying the medial origin of the dorsal longitudinal fasciculus and the dorsal path of the stria terminalis that originates at the VMH. In still other embodiments, the number of brain structures used as a reference to establish the location of the first brain structure may be greater than one brain structure. For example, the nerve tracts leading to a second and third brain structure are followed to identify the location of the second and third brain structure. The location of the first brain structure is then identified with reference to the location of the second and third brain structure. In still other embodiments, more than two brain structures may be used to establish reference points for identification of the location of the first brain structure.

II. Overview of the Energy Homeostasis System

The energy-homeostasis system includes both hypothalamic and extra-hypothalamic centers that are involved in processes regulating both the energy intake ($E_{IN}$) and the total energy expenditure (TEE). While $E_{IN}$ has one component, food intake ($F_{IN}$), the TEE can be divided into two main components: the energy expended due to movement-related activities and the energy expended due to non-movement-related activities. This division is such that at any given time the sum of these two components is equal to the TEE. In various aspects, the movement-related energy expenditure can be the mechanical energy expenditure (MEE) and the non-mechanical energy expenditure (nMEE) as the difference between the TEE and the MEE (Harnack et al., *Journal of Neuroscience Methods*). In humans the nMEE represents up to 70% of the TEE (McClean et al, *Animal and Human Calorimetry*). The fact that body weight (BW) remains relatively constant is due to the proper regulation of the nMEE.

Several mutually interacting hypothalamic nuclei may influence the MEE by inducing a change in spontaneous locomotor activity (Castenada et al., *Journal of Nutrition*) and shivering thermogenesis (Thornhill et al., *Canadian Journal of Physiology and Pharmacology*). These same mutually interacting hypothalamic nuclei may also regulate both the $F_{IN}$ and the nMEE through a net of complexly-interacting nuclei described below.

As can be understood from FIG. 1, at least five hypothalamic nuclei: Arcuate Nucleus (ARC) 5, Paraventricular (PVN) 10, Ventromedial Hypothalamic Nucleus (VMH) 15, Dorsomedial Hypothalamic Nucleus (DMH) 20 and the Lateral Hypothalamic Area (LHA) 25, may be involved in the regulation of the $F_{IN}$ and the nMEE. Some of the afferent and efferent connections to and from these nuclei and their molecular mechanisms are described in more detail below. In addition, at least part of the nMEE regulation may be exerted via sympathetic and parasympathetic modulation (Berthoud, *Neuroscience and Biobehavioral Reviews*). Indirect connections between hypothalamic nuclei and the vagus nerve via the nucleus of the solitary tract (NTS) may also provide signals that influence the $F_{IN}$.

a. The Arcuate Nucleus (ARC)

As shown in FIG. 1, the ARC 5, located at the inferior medial tuberal hypothalamic region, receives information from circulating molecules due to a leaky blood-brain-barrier in the area (at the median eminence) (Broadwell et al., *Journal of Comparative Neurology*), and from direct neuronal inputs. The ARC 5 may act as both an integrative center and a command center for the energy homeostasis system 2. In particular, signaling-molecules circulating in the blood are monitored to detect whether long-term energy (e.g. leptin), middle-term energy (e.g. insulin) and/or short-term energy (e.g. glucose and ghrelin) is available (Berthoud, *Neuroscience and Biobehavioral Reviews*; Bagnol, *Current Opinion in Drug Discovery and Development*). Generally, leptin, which is produced by adipose tissue, circulates in the blood stream in a concentration that is proportional to the amount of total body-fat tissue. Under abnormal circumstances, leptin concentration in the blood may be transiently uncorrelated to the total body-fat content (Kennedy et al., *Journal of Clinical Endocrinology and Metabolism*). The concentration of ghrelin, a hormone produced in the epithelial cells in the stomach (Wynne, *Journal of Endocrinology*), is at its lowest point after a meal, and the concentration level may increase until the next meal (Cowley, *Neuron*). The ARC 5 receives neuronal inputs from regions inside and outside the hypothalamus. Its intra-hypothalamic afferents originate mainly at the PVN 10, the LHA 25 and the VMH 15. Most of its extra-hypothalamic afferents originate at the NTS 30 (also known as the solitary nucleus), the amygdala, and the bed nucleus of the striaterminalis (Berthoud, *Neuroscience and Biobehavioral Reviews*; DeFalco et al., *Science*).

The ARC 5 may include at least two different neuronal populations that produce functionally antagonistic signaling molecules. One population produces pro-energy-conserving signaling molecules (ECm) and the other population produces pro-energy-expending signaling molecules (EEm). To regulate both $F_{IN}$ and nMEE, these signaling molecules influence neuronal activity in other hypothalamic nuclei and in the ARC 5 (Williams et al., *Physiology & Behavior*). The pro-energy-conserving population produces neuropeptide-Y (NPY) and agouti gene-related peptide (AgRP), both of which possess potent energy-conserving effects (Hahn et al., *Nature Neuroscience*; Broberger, *Proceedings of the National Academy of Sciences of the United States of*

*America*). The pro-energy-expending population produces pro-opiomelanocortin (POMC) and cocaine-and-amphetamine regulated transcript (CART) (Elias et al., *Neuron*; Kristensen, *Nature*). The POMC is a precursor to the α-melanocyte-stimulating hormone (α-MSH), and both the α-MSH and CART reduce FIN and increase nMEE. The production of NPY/AgRP may be inhibited by NPY (NPY-Y2 receptor) (Broberger et al., *Neuroendocrinology*), α-MSH (ARC MC3 receptor) (Jobst et al., *Trends in Endocrinology and Metabolism*), leptin (Baskin et al., *Journal of Histochemistry & Cytochemistry*; Mercer et al., *Journal of Neuroendocrinology*), and insulin (Wang et al., *Brain Research*). The production of NPY/AgRP may be promoted by orexin (ORX) which is produced in the LHA 25 (Guan et al., *Neuroreport*; Horvath et al., *Journal of Neuroscience*; Peyron et al., *Journal of Neuroscience*), by ghrelin (Wynne, *Journal of Endocrinology*), and by circulating glucocorticoids (Williams et al., *Physiology & Behavior*). The production of POMC/CART may be decreased by α-MSH (ARC MC3 receptor) (Jobst et al., *Trends in Endocrinology and Metabolism*) and increased by leptin (Jobst et al., *Trends in Endocrinology and Metabolism*). However, medial VMH neurons, which may be directly or indirectly stimulated by POMC, send excitatory projections to POMC neurons in the ARC 5 (Sternson et al., *Nature Neuroscience*) thereby driving the melanocortin system.

The efferent pathways of these populations project mainly into other hypothalamic nuclei but also to extra-hypothalamic regions (Broberger et al., *Proceedings of the National Academy of Sciences of the United States of America*; Broberger et al., *Physiology & Behavior*). Efferent connections of the NPY/AgRP population project to the PVN 10, LHA 25, DMH 20, and VMH 15 (Berthoud et al., *Neuroscience and Biobehavioral Reviews*; Wynne et al., *Journal of Endocrinology*; Williams et al., *Physiology & Behavior*). Efferent connections to the POMC/CART population projects to the LHA 25 (e.g. into ORX producing neurons) (Elias et al., *Neuron*) and DMH 20 (e.g. NPY producing neurons). The POMC/CART-ARC neurons have direct projections to the VMH 15 (Wynne et al., *Journal of Endocrinology*; Guan et al., *Molecular Brain Research*) and the latter has numerous melanocortin receptors to which POMC binds (e.g. MC4r and MC3r) (Berthoud et al., *Neuroscience and Biobehavioral Reviews*; Bagnol et al., *Current Opinion in Drug Discovery & Development*; Wynne et al., *Journal of Endocrinology*).

The ARC may be identified and located for targeting with reference to the VMH and one or more nerve tracts. The nerve tracts include, but are not limited to, the stria terminalis. The stria terminalis may be identified by DTI, and additional images are then taken to follow the tract into the VMH. The location of the ARC may then be determined relative to the location of the VMH. After selecting a reference, the location of the ARC can be established by a set of 3D coordinates, and then targeted (either the structure or the fiber tracts leading thereto may be modulated (inhibited or excited)) for a neuromodulation therapy, such therapy including but not limited to, electric, magnetic, ultrasound, and local drug delivery. The neuromodulation therapy may include, but is not limited to, modulation of the neural activity of a particular nucleus or modulating the activity of a particular nucleus by modulating the activity of the fiber tracts directly or indirectly connected thereto.

In summary, the neuronal activity in the ARC 5 tends to balance the TEE and the FIN. The ARC 5 monitors the energy status in the body and may act upon other hypothalamic nuclei in order to compensate for an imbalance in the energy system.

b. Paraventricular Nucleus (PVN)

The PVN 10 is located in the superior periventricular chiasmatic hypothalamic region. The PVN 10 is involved in several regulatory systems including the energy-homeostasis system. A decrease in the $F_{IN}$ and an increase in nMEE, caused by the electrical stimulation of the PVN 10, appears to be mediated by the potentiation of GABA-ergic interneurons. Afferent projections from the ARC 5 and from the DMH 20 that release NPY/AgRP and NPY respectively, inhibit GABA-releasing interneurons. The POMC/CART projections increase GABA release from the same interneurons into the PVN 10 (Cowley et al. *Neuron*). Other afferent projections into the PVN 10 originate at ORX-producing neurons in the LHA 25. These LHA-neurons may mediate their effect through the orexin receptor-2 (OX2r), which is abundant in the PVN 10 (Bagnol et al. *Current Opinion in Drug discovery & Development*). OX2r may modulate arousal in sleep-wakefulness cycles (Lin et al., *Cell*) but may not modulate $F_{IN}$ because $F_{IN}$ is affected by OXR acting upon OX1r (Lecea et al., *Proceedings of the National Academy of Sciences of the United States of America*; Haynes et al., *Peptides*). Non-endocrine efferents from the PVN 10 project to several hypothalamic nuclei, including the ARC 5, VMH 15, DMH 20, and LHA 25 (Terhorst et al., *Brain Research Bulletin*). Extrahypothalamic efferent projections from the PVN 10 terminate in the NTS 30 and in the preganglionic neurons. The projections that terminate in the NTS 30 trigger neuronal activity that exert an inhibitory effect in the dorsal motor nucleus (Zhang et al., *American Journal of Physiology-Gastrointestinal and Liver Physiology*). In turn, the dorsal motor nucleus has an excitatory effect on the autonomic nervous system (ANS) (Nishimura et al., *Journal of Neurophysiology*).

In summary, the PVN 10 receives inputs from and sends outputs to most hypothalamic nuclei involved in the energy-homeostasis system 2. The PVN 10 also projects to both sympathetic and parasympathetic neurons and thereby functions as an integrating, processing, and actuating center for the energy-homeostasis system 2.

The PVN may be identified and located for targeting with reference to one or more nerve tracts. The nerve tracts include, but are not limited to, the hypothalamic-hypophyseal tract. The hypothalamic-hypophyseal tract runs from the PVN to the posterior lobe of the pituitary gland. After selecting a reference, the location of the PVN can be established by a set of 3D coordinates, and then targeted (either the structure or the fiber tracts leading thereto may be modulated (inhibited or excited)) for a neuromodulation therapy, such therapy including but not limited to, electric, magnetic, ultrasound, and local drug delivery. The neuromodulation therapy may include, but is not limited to, modulation of the neural activity of a particular nucleus or modulating the activity of a particular nucleus by modulating the activity of the fiber tracts directly or indirectly connected thereto.

c. Ventromedial Hypothalamic Nucleus (VMH)

The VMH 15 is located in the medial tuberal hypothalamic region. The VMH 15 has been implicated in metabolic (Ruffin et al., *Brain Research*), reproductive (Nishimura et al., *Journal of Neurophysiology*), affective (Kruk, *Neuroscience and Biobehavioral Reviews*), and locomotor (Narita et al., *Behav. Brain Res.*) behavior. The VMH 15 may be anatomically divided into four regions that may be only slightly connected or completely unconnected. These four regions are the anterior VMH (aVMH), ventrolateral VMH (vlVMH), central VMH (cVMH), and dorsomedial VMH (dmVMH) (Canteras et al., *Journal of Comparitive Neurology*).

Within the energy-homeostasis system, the VMH 15 has been referred to as the "satiety center" (Schwartz et al., *Nature*). In addition, stimulation of the VMH may increase locomotor activity (Narita et al., *Behav. Brain Res.*), non-mechanical energy expenditure (nMEE), decrease $F_{IN}$ (Ruffin et al., *Brain Research*), promote lipolysis (Ruffin et al., *Brain Research*; Takahashi et al. *J. of the Autonomic Nervous System*; Shimazu, *Diabetologia*), and stimulate non-shivering thermogenesis (Thornhill et al., *Brain Research*). Experiments have also shown that VMH activity may regulate glucose uptake in skeletal muscles during exercise (Vissing et al., *American Journal of Physiology*) and that lesions in the VMH 15 may produce obesity and hyperphagia (Williams et al., *Physiology & Behavior*). The activity in the VMH may be influenced by both short and long-term energy availability because it contains numerous leptin receptors (Shioda et al., *Neuroscience Letters*) and close to half of its neurons are stimulated by a glucose increase (Ashford et al., *Pflugers Archiv-European Journal of Physiology*; DunnMeynell et al., *Brain Research*; Muroya et al., *Neuroscience Letters*). In particular, the activity of the gluco-sensitive neurons in the VMH 15 is up-regulated by leptin and down-regulated by ORX (originating in the LHA) (Shiraishi et al., *Physiology & Behavior*).

The VMH 15 receives afferent projections from the ARC 5 (e.g. NPY/AgRP and POMC/CART neurons) (Wynne et al., *Journal of Endocrinology*), the LHA 25 (e.g. ORX and melanin-concentrating hormone neurons) (Jobst et al., *Trends in Endocrinology and Metabolism*), the DMH 20, the PVN 10, the ANH (Terhorst et al., *Brain Research Bulletin*), and the NTS 30 (Fulwiler et al., *Neuroscience Letters*). In addition to projecting efferent fibers to all of the above nuclei, the VMH 15 also projects to the PHA, the zona incerta (ZI), limbic areas, several thalamic nuclei, the amygdala, the periaqueductal gray, and to the entorhinal area (Canteras, et al., *Journal of Comparative Neurology*). Medial VMH neurons, which may be influenced by POMC produced by ARC neurons, send excitatory projections to POMC neurons in the ARC (Sternson et al., *Nature Neuroscience*) which may help to drive the melanocortin system.

1. Identification of the dmVMH

The dmVMH may be identified with reference to one or more nerve tracts. The nerve tracts include, but are not limited to, the stria terminalis, the dorsal longitudinal fasciculus, the fornix and the mammilothalamic tract. By identifying these tracts, the location of the dmVMH may be identified and may be targeted for a neuromodulation therapy, such therapy including but not limited to, electric, magnetic, ultrasound, and local drug delivery.

In some embodiments, the stria terminalis and the dorsal longitudinal fasciculus nerve tracts are recognized and their terminations identified. A branch of the stria terminalis carries fibers from the VMH to the amygdala located dorsally from the VMH and arching around the thalamus. The dorsal longitudinal fasciculus originates in the hypothalamic nuclei located medially around the third ventricle and then travels posteriorly before turning ventrally. The location of the dmVMH may be determined by identifying the medial origin of the dorsal longitudinal fasciculus and the dorsal path of the stria terminalis that originates at the VMH. In some embodiments, identifying the stria terminalis may be sufficient to successfully determine the location of the dmVMH.

In some embodiments, the fornix and the mammillothalamic tract may be used to determine the location of the dmVMH. The fornix, projecting from the hippocampi to the mammillary bodies, travels through the hypothalamus and marks a separation between the medial and the lateral hypothalamus. The mammillothalamic tract projects from the mammillary bodies to the anterior nuclei of the dorsal thalamus. The relative location of the fornix and the mammilothalamic tract can be used as a reference to identify and target the dmVMH. After selecting a reference, the location of the dmVMH (or other region/portion of the VMH) can be established by a set of 3D coordinates, and then targeted (either the structure or the fiber tracts leading thereto may be modulated (inhibited or excited) for a neuromodulation therapy, such therapy including but not limited to, electric, magnetic, ultrasound, and local drug delivery. The neuromodulation therapy may include, but is not limited to, modulation of the neural activity of a particular nucleus or modulating the activity of a particular nucleus by modulating the activity of the fiber tracts directly or indirectly connected thereto.

In summary, the VMH 15 is anatomically divided and these divisions may be functionally different. With respect to the energy-homeostasis system, the VMH 15 integrates information about short-term and long-term energy availability and it may have functional connections with most of the other hypothalamic nuclei involved in the energy-homeostasis system. Thus, VMH activity may influence $F_{IN}$, MEE, nMEE, lipolysis, and glucose uptake in muscles.

d. Dorsomedial Hypothalamic Nucleus (DMH)

The DMH 20 is located in the medial tuberal region just dorsal to the VMH 15. Lesions in the DMH may cause changes in pancreatic-nerve activity (Elmquist et al., *Proceedings of the National Academy of Sciences of the United States of America*) and may induce hypophagia, thereby leading to a lower body weight (BW) (Bernardis et al., *Proceedings of the Society for Experimental Biology and Medicine*) and stimulation of the DMH may result in hyperglycemia (Elmquist et al., *Proceedings of the National Academy of Sciences of the United States of America*). These effects may be carried out via NPY-expressing neurons in the DMH that project to the PVN (Berthoud, *Neuroscience and Biobehavioral Reviews*).

From within the hypothalamus, the DMH 20 receives afferent projections from the VMH 15, the LHA 25, the ARC 5, and the anterior hypothalamic nucleus (AHN). From outside the hypothalamus, the DMH 20 may receive afferent projections from the periaqueductal gray, the hippocampal formation (e.g. ventral subiculum) and from the prefrontal cortex (Thompson et al., *Brain Research Reviews*). In addition, the DMH 20 may receive inputs for leptin and insulin receptors as well as from gluco-sensitive neurons expressed in the nucleus. The DMH 20 projects mainly to other hypothalamic nuclei, in particular to the PVN 10 but may also project to the VMH 15 and to the AHN, among others.

In summary, the DMH 20 may constitute an integrative center for intra- and extra-hypothalamic inputs that modulate aspects of the energy-homeostasis system, and such modulation may occur by influencing PVN 10 activity.

e. Lateral Hypothalamic Area (LHA)

The LHA 25 has extensive connections both inside and outside the hypothalamus. It sends and receives projections to and from the cortex, the thalamus, the basal ganglia, the mid-brain, the hippocampal formation, the NTS 30, and most hypothalamic regions (Berthoud, *Neuroscience and Biobehavioral Reviews*; Wynne et al., *Journal of Endocrinology*; Williams et al., *Physiology & Behavior*; Jobst et al.,

*Trends in Endocrinology and Metabolism*). In particular, information from the GI tract reaches the LHA 25 via the NTS 30 (Woods, *AJP-Gastrointestinal and Liver Physiology*).

The LHA may also receive information from circulation through leptin receptors (Elmquist, *Neuroendocrinology of Leptin*) and numerous gluco-sensing neurons that increase their firing rate in response to a decrease in circulating glucose (Ashford et al., *Pflugers Archiv-European Journal of Physiology*). In particular, a decrease in glucose may cause an increase in ORX production in the LHA 25 (Hakansson et al., *Journal of Neuroendocrinology*; Chemelli et al. *Cell*), which in turn may stimulate $F_{IN}$ acutely (Bayer et al., *Neuroreport*). There are two types of ORX molecules produced in the LHA 25, Orexin-A (ORXa) and Orexin-B (ORXb) (Peyron et al., *Journal of Neuroscience*; Sakurai et al., *Cell*) and two receptors have been found to which ORX binds: OX1R and OX2R. The OX1R may have a much higher affinity (approximately 10-fold) for ORXa than for ORXb, while the other ORX receptor, OX2R, may have similar affinities for both ORXa and ORXb (Lund et al., *Journal of Biological Chemistry*). Experimental data suggests that only ORXa is directly related to the energy-homeostasis system. Intraventricular injections of ORXa may acutely promote feeding (de Lecea et al., *Proceedings of the National Academy of Sciences of the United States of America*; Haynes et al., *Peptides*), and blocking its effects with a specific antagonist may reduce $F_{IN}$ (Yamada et al., *Biochemical and Biophysical Research Communications*). ORXb may play an important role in the arousal part of the sleep-wakefulness cycle, as shown by OX2R knockout-mice experiments in which the animals develop narcolepsy (Chemelli et al. *Cell*). In contrast to the VMH, where OX1R is heavily expressed, the PVN contains a substantial amount of OX2R (Bagnol, *Current Opinion in Drug Discovery & Development*). In the VMH 15, ORXa may inhibit the activity of gluco-sensitive neurons thus attenuating the response of the VMH 15 to an increase in the circulating glucose (Shiraishi et al., *Physiology & Behavior*). Experimental data suggests that both OX1R and OX2R are expressed in the ARC where they modulate, for example, NPY/AgRP and POMC/CART neurons (Burdakov et al., *Journal of Neuroscience*; Suzuki et al., *Neuroscience Letters*).

In summary, the LHA 25 receives information from many systems including the GI tract. The LHA 25 integrates information from all of these systems, and in turn, influences the expression of ECm and EEm in the ARC 5 as well as the glucose sensitivity in the VMH 15.

The LHA may be identified with reference to one or more nerve tracts. The nerve tracts include, but are not limited to, the ventral amygdalofungal pathway, the medial forebrain bundle, the dorsal longitudinal bundle and the fornix. In some embodiments, the ventral amygdalofungal pathway, the medial forebrain bundle, the dorsal longitudinal bundle and the fornix are used to identify the LHA. The LHA is flanked or traversed laterally by the medial forebrain bundle and the dorsal longitudinal bundle is located dorso-medially with respect to the LHA. The ventral amygdalofungal pathway goes into the LHA. The fornix can be considered as the boundary between the medial and lateral hypothalamus. The medial forebrain bundle runs between the ventral tegmentum and the nucleus accumbens passing by the LHA. After selecting a reference (e.g. a nerve tract or the brain structure), the location of the LHA can be established by a set of 3D coordinates, and then targeted (either the structure or the fiber tracts leading thereto may be modulated (inhibited or excited)) for a neuromodulation therapy, such therapy including but not limited to, electric, magnetic, ultrasound, and local drug delivery. The neuromodulation therapy may include, but is not limited to, modulation of the neural activity of a particular nucleus or modulating the activity of a particular nucleus by modulating the activity of the fiber tracts directly or indirectly connected thereto.

f. The Perifornical Region (Pe)

The Perifornical (Pe) region, especially lateral and dorsolateral to the fornix, is an important site related to food intake. This region receives afferent connections from the pontine parabrachial nucleus and bed nucleus of the stria terminalis (BNSt), both of which are involved in gustatory function. The Pe sends efferent connections to the solitary nucleus (NTS), the parabrachial nucleus, BNSt, and the central nucleus of the amygdala, all of which are also involved in gustatory functions. In addition, the Pe has both afferent and efferent connections with the Ventral Tegmental Area (VTA), which, in turn, is part of the meso-accumbens dopaminergic circuit that is important in the feeding reward mechanism.

The Pe region may be identified with reference to one or more nerve tracts. The nerve tracts may include the fornix and the amygdalofungal pathway. The fornix, projecting from the hippocampi to the mammillary bodies, travels through the hypothalamus separating the medial and the lateral hypothalamus. The ventral amygdalofungal pathway projecting from the amygdala has two main paths, one to the lateral hypothalamic area and a second one to the dorsomedial nucleus of the thalamus. The desired target area is in the LHA in close proximity to the fornix. The target can be located by identifying the fornix and then selecting the anterior-posterior position by the relative position of the ventral amygdalofungal pathway. The relative location of the nerve tracts can be used to target the Pe. After selecting a reference, the location of the Pe can be established by a set of 3D coordinates and then targeted (either the structure or the fiber tracts leading thereto may be modulated (inhibited or excited)) for a neuromodulation therapy, such therapy including but not limited to, electric, magnetic, ultrasound, and local drug delivery. The neuromodulation therapy may include, but is not limited to, modulation of the neural activity of a particular nucleus or modulating the activity of a particular nucleus by modulating the activity of the fiber tracts directly or indirectly connected thereto.

III. The Subgenual Area

Empirical observations show that the subgenual area, also called brodmann area 25 (BA25), is over active in many clinically depressed patients (Mayberg et al., 2005).

As can be understood from FIG. 5 (which is reproduced from Walter J. Hendelman, Atlas of Functional Neuroanatomy, $2^{nd}$ ed. Published/distributed: Boca Raton, Fla.: CRC Taylor & Francis, 2006), and which depicts a view of the brain wherein the subgenual area is shown, BA25 is part of the cingulate region in the cerebral cortex. In humans, it is a strip in the caudal portion of the subcallosal area adjacent to the paraterminal gyrus.

Areas such as the brainstem, hypothalamus, and insula, which are associated with behaviors that are altered in clinically depressed people, are connected to BA25. Among those behaviors are sleep, appetite, libido, and neuroendocrine regulation. In addition, autonomic processes affecting motivation/reward and memory/learning mechanisms, which are impacted in depression, are modulated by the multiple neural pathways linking BA25 to orbitofrontal, medial prefrontal, and parts of the anterior and posterior cingulate cortices (Mayberg et al., 2005).

BA25 may be identified with reference to one or more nerve tracts. The nerve tracts may include the Cingulate Gyrus fibers. The Cingulate Gyrus fibers are passing adjacent to the subgenual area as they traverse frontal fibers nearby. The target area can be identified by locating the Cingulate Gyrus fibers and following the fibers until they pass an area adjacent to the subgenual area. Thus, the relative location of the fibers can be used as a reference to target the subgenual area. After selecting a reference, the location of the subgenual area can be established by a set of 3D coordinates and then targeted (or the nerve tracts related thereto may be targeted) for a neuromodulation therapy, such therapy including but not limited to, electric, magnetic, ultrasound, and local drug delivery. The neuromodulation therapy may include, but is not limited to, modulation of the neural activity of a particular nucleus or modulating the activity of a particular nucleus by modulating the activity of the fiber tracts connected thereto.

IV. The Nucleus Accumbens

As can be understood from FIG. 5, the nucleus accumbens is located approximately where the anterior portion of the putamen and the head of the caudate meet just lateral to the septum pellucidum. The olfactory tubercle and the nucleus accumbens together form a part of the basal ganglia—the ventral striatum. Without wishing to be bound by theory, it is thought that the nucleus accumbens may play an important role in pleasure, laughter, reward, addiction, the placebo effect, fear and aggression.

The medium spiny neuron is the primary neuronal cell type found in the nucleus accumbens and these neurons are also the output or main projection neurons of the nucleus accumbens. One of the main inhibitory neurotransmitters of the CNS, gamma-aminobutyric acid (GABA) is the neurotransmitter produced by the medium spiny neuron.

The nucleus accumbens may be identified with reference to one or more nerve tracts. The output neurons send axon projections to the ventral analog of the globus pallidus, also known as the ventral pallidum. The ventral pallidum projects to the medial dorsal nucleus of the dorsal thalamus, which in turn projects to the prefrontal cortex as well as the striatum. Other efferents from the nucleus accumbens may include connections with the pontine reticular formation and the substantia nigra. The main inputs into the nucleus accumbens include the basolateral amygdala, prefrontal association cortices and the dopaminergic neurons located in the ventral tegmental area (VTA), which connect via the mesolimbic pathway. (See generally, http://en.wikipedia.org/wiki/nucleus_accumbens).

The target area can be identified by locating one or more of the above identified fibers and following the fibers until they pass an area adjacent to or into the nucleus accumbens. Thus, the relative location of the fibers can be used as a reference to target the nucleus accumbens. After selecting a reference, the location of the nucleus accumbens can be established by a set of 3D coordinates and then targeted (or the nerve tracts related thereto may be targeted) for a neuromodulation therapy, such therapy including but not limited to, electric, magnetic, ultrasound, and local drug delivery. The neuromodulation therapy may be used to treat, for example only, depression, obsessive compulsive disorder (OCD), or addiction. The neuromodulation therapy may include, but is not limited to, modulation of the neural activity of a particular nucleus or modulating the activity of a particular nucleus by modulating the activity of the fiber tracts directly or indirectly related thereto. In one embodiment using DTI MRI, the medial forebrain bundle, which runs between the ventral tegmentum and the nucleus accumbens passing by the LHA, can be targeted at various locations along its path.

V. The Subthalamic Nucleus (STN)

Figure 6A:
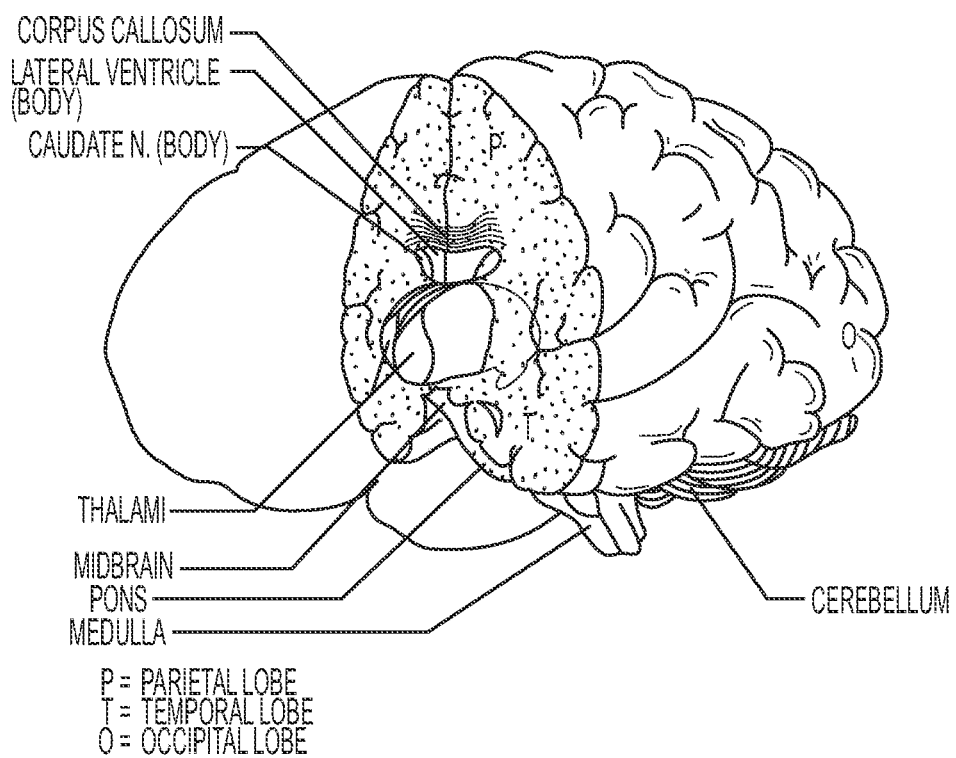
FIG. 6A depicts an additional view of several brain regions and brain structures.
Figure 6B:
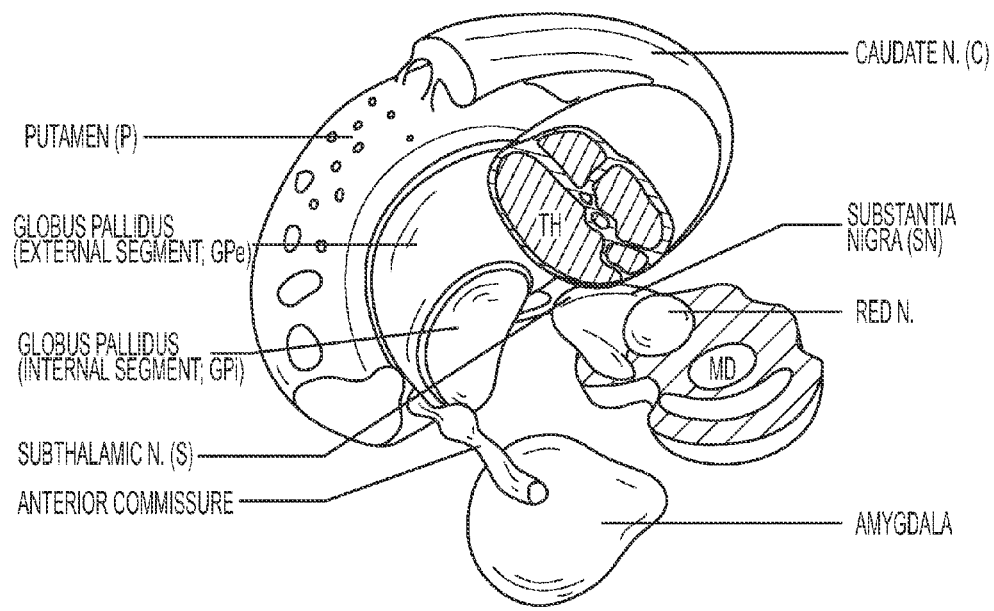
FIG. 6B depicts a portion of the of the several brain regions and brain structures of FIG. 6A.
Figure 6C:
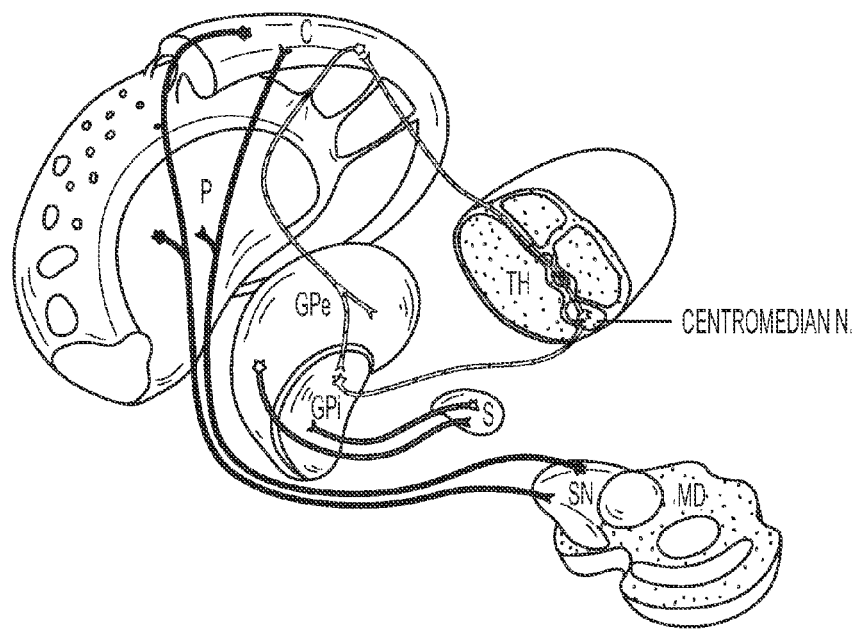
FIG. 6C depicts an expanded view of the brain regions and brain structures of FIG. 6B, wherein nerve tracts found therein are also shown.

As can be understood from FIGS. 6A-6C (which are reproduced from Walter J. Hendelman, Atlas of Functional Neuroanatomy, $2^{nd}$ ed. Published/distributed: Boca Raton, Fla.: CRC Taylor & Francis, 2006), which depict various brain regions, brain structures and nerve tracts, including the subthalamic nucleus, the STN is part of the brain stem and receives afferent connections from the primary motor area of the cerebral cortex, and the globus pallidus and in turn sends efferent back to the globus pallidus and the substantia nigra. The STN is part of a neural circuit, which greatly influences motor control. In illnesses such as Parkinson's Disease, a decrease in dopamine production in the Substantia Nigra generates a cascade of effects throughout the above-mentioned motor-control circuit leading to an overactive STN partially resulting in the characteristic tremor observed in Parkinson's patients.

In some embodiments, electrical stimulation at frequencies ranging between 100 Hz and 150 Hz in the dorsolateral portion of the STN may mitigate some of Parkinson's symptoms. In other embodiments, higher frequencies may be used.

The STN, and in particular its dorsolateral portion, may be identified with reference to one or more nerve tracts. The nerve tracts may include the ansa lenticularis (AL), the lenticular fasciculus (LF), subthalamic-occipitoparietal fibers, frontal fibers traversing the internal capsule, and the dentorubrothalamic fascicle. The AL pathway lays rostral to the NTS and the LF limits the NTS dorsally; passing above the NTS in a latero-medial trajectory. The subthalamic-occipitoparietal fibers intersect the dorsal portion of the STN. In one embodiment, the LF and the subthalamic-occipitoparietal fibers can be used to delimit the dorsolateral aspect of the STN. The target area can be identified by locating one or more of the nerve tracts and following the tracts into the STN or to a location near the STN. Thus, the relative location of the nerve tracts can be used as a reference to target the STN. After selecting a reference, the location of the STN can be established by a set of 3D coordinates and then targeted (either the STN or the nerve tracts related thereto) for a neuromodulation therapy, such therapy including but not limited to, electric, magnetic, ultrasound, and local drug delivery.

In some embodiments, the methods disclosed herein utilize an imaging technique known as Diffusion Tensor Imaging (DTI) to identify nerve tracts (also called fiber tracts). DTI provides a non-invasive and non-destructive technique to follow nerve tracts in humans.

VI. Diffusion Imaging

Diffusion is a random molecular motion in which there is a net transfer of molecules from an area of higher concentration to an area of lower concentration. It is also known as Brownian motion. Diffusion weighted imaging (DWI) uses the theory of Brownian motion of water molecules in biological tissues, such as brain structures. However, because biological tissues have structure, diffusion is not truly random in biological tissue. Thus, water diffusion in these structures is referred to as an "apparent diffusion" coefficient (ADC). Diffusion MRI is a magnetic resonance imaging (MRI) method or technique that produces in vivo images of biological tissues weighted with local microstructural characteristics of water diffusion. In order to obtain the diffusion weighted images, at least two strong gradient pulses are added to the MRI pulse sequence. The intensity of the image is attenuated at each position depending on the direction and strength (b-value) of the magnetic diffusion gradient and on the local microstructure upon which the molecules of water diffuse. In general, the diffusion in the direction of the diffusion gradient is directly proportional to the attenuation of the image at a particular position. The MRI scans are repeated, applying different directions and/or strengths of the diffusion gradient for each scan such that the tissue's complete diffusion profile can be measured. In general, the image intensity may vary when the diffusion gradient or spatial direction is changed. In order to account for the changes, a diffusion tensor model may be used.

Diffusion Tensor Imaging (DTI) is the measure of tensor directly from diffusion weighted data. A tensor may be used to describe diffusion in anisotropic systems. By applying, in at least six directions, a diffusion gradient in diffusion MRI, a tensor (a 3×3 matrix) may be calculated to describe the three-dimensional shape of diffusion. From DTI, the location, anisotropy and orientation of the nerve tracts of the brain can be visualized. That is, the diffusion tensor's principal direction may be used to determine the nerve tracts making the connection between different brain regions. The nerve tracts direction may be indicated by the tensor's main eigenvector. The connectivity of the brain may be used to determine, for example, how the brain structures are interconnected. For example, multiple images or sets of images may be taken in order to follow the nerve tracts from a first point to a second point. In some brain regions, it may be difficult to visualize a particular tract. In such a situation, the first DTI may be taken in the non-target region where the chosen tract is easily identified (e.g. it may be the largest tract in that region). Additional DTI are taken to follow the tract into the target region and to the target brain structure. As a non-limiting example, the first image may be taken at the dorsal boundary of the thalamus where the stria terminalis can be found. Additional images may be taken to follow the stria terminalis into the hypothalamus and then into the dorsal VMH. The medial portion of the dorsal VMH, the dmVMH, can be targeted by aiming the imager medially with respect to where the stria terminalis enters the dorsal VMH.

VII. Choosing the Reference

The reference or best available reference can be chosen by using, for example, a stereotactic frame, a "frameless" stereotactic device, anatomical references or other appropriate reference. Stereotactic surgery works on the basis of three main components: 1) a stereotactic planning system, including atlas, multimodality image matching tools, coordinates calculator, etc, 2) a stereotactic device or apparatus and 3) a stereotactic localization and placement procedure. Stereotactic frame guidance and techniques, such as CT imaging, MRI targeting and microelectrode recording may be used to place chronic stimulating electrodes in the targeted area.

Modern stereotactic planning systems are computer based. The stereotactic atlas is a series of cross sections of anatomical structure (e.g. of the human brain), depicted in reference to a two-coordinate frame. Thus, each brain structure can be easily assigned a range of three coordinate numbers, which will be used for positioning the stereotactic device. In most atlases, the three dimensions are: latero-lateral (x), dorso-ventral (y) and rostro-caudal (z).

The stereotactic apparatus uses a set of three coordinates (x, y and z) in an orthogonal frame of reference (cartesian coordinates), or, alternatively, a polar coordinates system, also with three coordinates: angle, depth and antero-posterior location. The mechanical device has head-holding clamps and bars which puts the head in a fixed position in reference to the coordinate system (the so-called zero or origin). In small laboratory animals, these are usually bone landmarks which are known to bear a constant spatial relation to soft tissue. For example, brain atlases often use the external auditory meatus, the inferior orbital ridges, the median point of the maxilla between the incisive teeth, or the bregma (confluence of sutures of frontal and parietal bones), as such landmarks. In humans, the reference points, as described above, are intracerebral structures which are clearly discernible in a radiograph or tomogram.

Guide bars in the x, y and z directions (or alternatively, in the polar coordinate holder), fitted with high precision vernier scales allow the neurosurgeon to position the point of a probe (an electrode, a cannula, etc.) inside the brain, at the calculated coordinates for the desired structure, through a small trephined hole in the skull.

Currently, a number of manufacturers produce stereotactic devices fitted for neurosurgery in humans, as well as for animal experimentation. Examples of such stereotactic devices include, Leksell Stereotactic Frame (Elekta, Atlanta, Ga.), CRW Stereotactic Frame (Integra Radionics, Burlington, Mass.) (for human use), large and small animal Stoelting stereotactic frame (Stoelting Co., Wood Dale, Ill.), large and small animal Stereotactic Instruments (Harvard Apparatus, Holliston, Mass.). An example of a "frameless" stereotactic device or a device used in a "frameless" surgery include VectorVision, made by BrainLAB of Westchester, Ill.

After identifying the target structure(s) and selecting a reference or the best available reference, the exact position of the target area is coded into 3D coordinates. These 3D coordinates may also be used to implant an electrode or direct the placement of a cannula to deliver a therapy and/or to collect information. The cannula or the implanted electrode may be used to modulate the activity of the brain structure. In some embodiments, the modulation of the activity of the identified and targeted brain structure is performed via implanted electrodes. In some embodiments, the modulation may be performed by Deep Brain Stimulation (DBS). In other embodiments, the modulation of the activity of the brain structure is performed via local drug delivery (which may be delivered via a cannula). In other embodiments, the modulation of the activity is performed by a combination of implanted electrodes and local drug delivery. In yet other embodiments, the modulation of the activity of the brain structure is performed via non-invasive methods such as ultrasound, transcranial magnetic stimulation (TMS), and/or energy beams that can change the temperature in the target tissue. Additionally, beam directed energy, either ionizing (DeSalles et al., *Acta Neurochir Suppl.*, 2008) or non-ionizing radiation (Tyler et al., PLOS One, 2008), may be used to modulate the brain circuitry.

VIII. Deep Brain Stimulation

Deep brain stimulation (DBS) is a surgical treatment involving the implantation of a medical device which sends electrical impulses to specific parts of the brain. In some embodiments, the device is referred to as a brain pacemaker. DBS directly modulates brain activity in a controlled manner. In various embodiments, its effects are reversible (unlike those of lesioning techniques).

Generally, the deep brain stimulation system includes three components: an implanted/implantable pulse generator (IPG), a lead, and an extension. The IPG is a pulse generator used to stimulate excitable tissue such as nerve tissue. The IPG can be battery-powered or inductibly-powered or powered by a combination of a battery and inductibly-transmitted energy. IPGs are often encased in a biocompatible hermetic housing, such as a titanium case.

When an IPG is used to stimulate brain tissue, electrical pulses are delivered to the brain to modulate neural activity at the target site. The IPG may be calibrated by a neurologist, nurse or trained technician to optimize symptom suppression and control side effects. At its proximal end, the lead is electrically connected to the IPG either directly or via the extension. At its distal end, the lead is in contact with the target tissue via at least one electrode or contact point. In some embodiments, the lead may be a coiled wire insulated in polyurethane with four platinum iridium electrodes and is placed in the target area of the brain.

Various commercial IPGs may be used in various embodiments of the present disclosure. For example, commercial embodiments known in the art can be used. In certain embodiments, IPGs that can be used include the Medtronic Soletra or Kinetra IPGs (Medtronic, Minn.), Libra (St. Jude, Minn.), used conventionally for DBS. Alternatively, a DBS developed to treat pain, such as the Restore and Restore Ultra IPGs (Medtronic, Minn.), Eon, Eon mini, Renew, or Genesis (St. Jude, Minn.), or Precision Plus (Boston Scientific Natick, Mass.). The IPG can be used for additional indications, including epilepsy (Responsive Neurostimulator system, Neuropace, Mountain View, Calif.), vagal neural signals (Maestro, Enteromedics St. Paul, Minn.), cochlear implants (Freedom, Cochlear Limited, Lane Cove, Australia), as well as other uses (Interstim II and Enterra, Medtronic, Minneapolis).

Examples of such DBS devices include, but are not limited to, devices designed for control of Parkinson's Syndrome, such as the Kinetra Model 7428 Neurostimulator or the Soletra Model 7426 Neurostimulators (Medtronic, Minn.). The power source(s) generate electrical signals that are transmitted to the brain via extensions. Examples of such extensions include, for example, Model 7482 Extensions or two Model 7495 Extensions (Soletra), or either two Model 3387 DBS Leads or two Model 3389 DBS Leads. Other devices can be used for tremor control therapy. Examples of these devices include power sources therapy which may include one single program Soletra Model 7426 Neurostimulator or one single program Model 7424 Itrel II Neurostimulator. The power source generates electrical signals that are transmitted to the brain via either one Model 7495 Extension or one Model 7482 Extension and either one Model 3387 DBS Lead or one Model 3389 DBS Lead. These components comprise the implantable portion of the Activa System for unilateral Activa Tremor Control Therapy (Medtronic, Minn.).

In various embodiments, an electrode may be inserted at the brain region to allow the brain region to be identified at a later time for therapeutic treatment. For example, a lead that contains an electrode is implanted after targeting a specific brain region. The electrode remains at least until such a time as DBS is applied.

In various embodiments, the IPG is configured to deliver DBS at one or more frequencies, or within a range of frequencies. The IPG can be configured to deliver electrical stimulation at frequencies less than, and/or greater than one or more of 50 Hz, 45 Hz, 40 Hz, 35 Hz, 30 Hz, 25 Hz, 20 Hz, 15 Hz, or 10 Hz. In various embodiments, the IPG can be configured to deliver electrical stimulation at frequencies greater than, and/or less than, one or more of 50 Hz, 60 Hz, 70 Hz, 80 Hz, 90 Hz, 100 Hz, 125 Hz, 150 Hz, 175 Hz, 200 Hz, 225 Hz, 250 Hz, 275 Hz, 300 Hz, 325 Hz, 350 Hz, 375 Hz, 400 Hz, 425 Hz, 450 Hz, 475 Hz, or 500 Hz. In various embodiments, the IPG can be configured to deliver electrical stimulation at a frequency greater than, and or less than, one of 500 Hz, 525 Hz, 550 Hz, 575 Hz, 600 Hz, 625 Hz, 650 Hz, 675 Hz, 700 Hz, 725 Hz, 750 Hz, 775 Hz, 800 Hz, 825 Hz, 850 Hz, 875 Hz, 900 Hz, 925 Hz, 950 Hz, or 975 Hz, or 1000 Hz. In various embodiments, the IPG can be configured to deliver electrical stimulation at greater and/or less than one or more of 1000 Hz, 2000 Hz, 3000 Hz, 4000 Hz, 5000 Hz, 6000 Hz, 7000 Hz, 8000 Hz, 9000 Hz, or 10000 Hz. In various embodiments, any of the above-referenced frequencies can be the upper or lower borders of an applied frequency.

The frequencies can be used for various embodiments. For example, depending on the particular neural system, lower frequencies tend to excite the neural elements (i.e. neural tissues), such neurons, axons, dendrites, nerve endings, nerve bundles, while higher frequencies tend to preferentially excite axons and in some cases inhibit neurons, and even higher frequencies tend to inhibit all neural elements. By way of example but not limitation, low frequency electrical stimulation may be used to produce a net excitatory effect, or alternatively to produce a net inhibitory effect.

In various embodiments, the IPG is configured to deliver DBS via different waveforms. For example, square monophasic, square biphasic with or without charge balanced, sinusoidal, ramp, triangular, exponential, and/or any combination of theses waveforms.

In various embodiments, the IPG is configured to deliver DBS at a specific pulse width or range of pulse widths. The IPG can be configured to deliver pulse widths in the range greater than and/or less than one or more of 10 μs, 20 μs, 30 μs, 40 μs, 50 μs, 60 μs, 70 μs, 80 μs, 90 μs, 100 μs, 125 μs, 150 μs, 175 μs, 200 μs, 225 μs, 250 μs, 275 μs, 300 μs, 325 μs, 350 μs, 375 μs, 400 μs, 425 μs, 450 μs, 475 μs, 500 μs, 525 μs, 550 μs, 575 μs, 600 μs, 625 μs, 650 μs, 675 μs, 700 μs, 725 μs, 850 μs, 875 μs, 900 μs, 925 μs, 950 μs, 975 μs, 1000 μs, 1500 μs, 2000 μs, 2500 μs, or 3000 μs. Those of skill in the art will recognized that one or more of the above times can be used as border of a range of pulse lengths. Pulse lengths can be defined in terms of extremely short pulses (i.e. between 10 and 50 μs), short pulses (i.e. between 50 to 350 μs), medium width pulses (i.e. between 350 to 700 μs), long pulses (i.e. between 700 us to 1.5 ms), very long pulses (i.e. between 1.5 to 3 ms), and extremely long pulses (i.e. >3 ms). Without being limited to any mechanism or mode of action, in certain cases longer pulses can excite fast and slower conducting neural elements such as smaller diameter axons as well as neurons for a given amplitude, while shorter pulses can excite fast conducting neural elements such as big diameter axons.

In various embodiments, the IPG is configured to deliver DBS electrical stimulation at a range of voltage or current amplitudes, which in various embodiments can be voltage controlled, current controlled, or a combination of both (i.e., the IPG produces current controlled pulses as well as voltage controlled pulses). In other embodiments, the amplitude can be applied by a capacitive discharge. In various embodiments, the amplitude can be in a range greater than and/or less than one or more of 5 μA, 6 μA, 7 μA, 8 μA, 9 μA, 10 μA, 20 μA, 30 μA, 40 μA, 50 μA, 60 μA, 70 μA, 80 μA, 90 μA, 100 μA, 125 μA, 150 μA, 175 μA, 200 μA, 225 μA, 250 μA, 275 μA, 300 μA, 325 μA, 350 μA, 375 μA, 400 μA, 425 μA, 450 μA, 475 μA, 500 μA, 525 μA, 550 μA, 575 μA, 600 μA, 625 μA, 650 μA, 675 μA, 700 μA, 725 μA, 850 μA, 875 μA, 900 μA, 925 μA, 950 μA, 975 μA, 1 mA, 2 mA, 3 mA, 4 mA, 5 mA, 6 mA, 7 mA, 8 mA, 9 mA, 10 mA, 20 mA, 30 mA, 40 mA or 50 mA. Those of skill in the art will recognized that one or more of the above amplitudes can be used as border of a range of amplitudes. Further, amplitudes can be described in terms of extremely low amplitudes (i.e. <10 uA and its equivalent voltage depending on the electrode(s)-tissue impedance), very low amplitudes (i.e. 10 to 100 uA and its equivalent voltage depending on the electrode(s)-tissue impedance), low amplitudes (i.e. 100 to 500 uA and its equivalent voltage depending on the electrode(s)-tissue impedance), medium amplitudes (i.e. 500 uA to 1 mA and its equivalent voltage depending on the electrode(s)-tissue impedance), high amplitudes (i.e. 1 mA to 5 mA and its equivalent voltage depending on the electrode(s)-tissue impedance), very high amplitudes (i.e. 5 mA to 10 mA and its equivalent voltage depending on the electrode(s)-tissue impedance), and extremely high amplitudes (i.e. >10 mA and its equivalent voltage depending on the electrode(s)-tissue impedance).

The actual amplitude can depend on several factors such as the distance between the electrode(s) and the target tissue, the distribution of the target tissue, the geometry of the electrode(s), the relative geometry and position between opposite and same polarity electrodes, the waveform, the actual polarity of the leading pulse, and other stimulation parameters such as frequency and pulse width. In order to reach a particular stimulation threshold (for a single neural element or for a given percentage of a population of neural elements such that a response is triggered), the amplitude, pulse width and frequency are not independent. In most cases the relationship between the amplitude, pulse width and frequency can be described by what is known in the art as strength-duration (S-D), strength-frequency (S-F), and strength-duration-frequency (S-D-F) curves, which can follow an exponential or hyperbolic mathematical form. The S-D-F curve is a 3 dimensional version of the better known 2 dimensional cases S-D and S-F curves.

In various embodiments, at least one of the IPG and lead of the DBS system are surgically implanted inside the body. In some embodiments at least one burr hole, which size can be any size known in the art which allows the placement and fixation of the at least one lead positioning and anchoring the lead correctly. The electrode is inserted, with instrumental feedback and/or feedback from the patient for optimal placement. In certain embodiments, the lead is connected to the IPG by the extension. In one embodiment, the extension is an insulated wire that runs from the head and down the side of the neck behind the ear to the IPG. In some embodiments, it may be placed subcutaneously below the clavicle. In some embodiments, it may be placed subcutaneously behind the abdomen, and in yet other embodiments where the IPG is cranially mounted, the extension may be placed subcutaneously in the head.

DBS leads are placed in the brain according to the type of symptoms to be addressed. For example, in non-Parkinsonian essential tremor, the lead is placed in the ventrointermedial nucleus (VIM) of the thalamus. For the treatment of dystonia and symptoms associated with Parkinson's disease (rigidity, bradykinesia/akinesia and tremor), the lead may be placed in either the globus pallidus or subthalamic nucleus. Methods of identifying these regions are also described in more detail herein.

IX. Verification of the Placement of the Electrode

When certain portions of the brain structure are stimulated, an immediate increase in energy expenditure (EE) and lipolysis is expected, e.g. when stimulating the dorsomedial portion of the VMH specifically. Therefore, in order to fine tune the location and/or identification of the brain structure, e.g., verify that the modulation is being applied to the desired targeted brain structure, at least one of the following may be monitored: a) the oxygen consumption (VO2), b) the energy expenditure (EE), c) the carbon dioxide production (VCO2), and d) the respiratory quotient (RQ=VCO2/VO2). As used herein, "fine-tune" means verifying the location and/or identification, and/or refine the identification of, the target structure.

In some experiments, as can be understood from the Examples found below, EE, VO2, VCO2, and RQ may be monitored using indirect calorimetry. Indirect calorimetry uses the overall oxygen consumption and the carbon dioxide production of a subject to estimate the rate at which the patient is expending energy, that is, indirect calorimetry is used to estimate the overall metabolic rate of the patient. The oxidation of each macro-nutrient (i.e. fats, carbohydrates and proteins) requires a specific amount of oxygen ($O_2$) and produces a specific amount of carbon-dioxide ($CO_2$), water ($H_2O$), and energy. The energy produced can be computed from the specific chemical reaction depending on the particular nutrient.

Using indirect calorimetry, an increase in lipolysis is signaled by a decrease in the RQ. When the target area is one that controls the overall metabolic rate and/or the percentage of oxidation of the main nutrients (i.e., carbohydrates, proteins, and fats), for example the VMH, indirect calorimetry may be used during the implantation procedure to fine tune the identification of the target. In this case, as the electrode approaches the coordinates of the target area, a small current is passed into the tissue through at least one electrode pole while indirect calorimetry is performed. Since indirect calorimetry measures the energy expenditure (i.e., the metabolic rate) as well as the respiratory quotient (RQ), the indirect calorimetry measurements can be used to signal when the target is reached. After the target region is reached, the electrode is fixed in place using standard neurosurgical techniques. The RQ changes when the oxidation-rate ratio carbohydrates/fats changes. The energy expenditure increases and RQ decreases when the dorsomedial portion of the VMH is stimulated with low-intensity currents. The energy expenditure may also increase if a larger current is used. In animal models, the RQ may increase (sometimes only transiently) as the current is increased. Protocols for implementation or performance of indirect calorimetry are known.

In other embodiments, verification of the location of the electrode may be by other objective measurements, such as a decrease or an absence of tremors in a Parkinson's patient. In still other embodiments, verification of the location of the electrode may be by subjective measurements, such as soliciting patient feedback such as asking for the patient's own assessment of a change in mood.

X. Obesity and the Energy Homeostasis System

The energy homeostasis system is involved in the regulation of appetite and metabolic rate (also called energy expenditure or total energy expenditure). Obesity is an energy imbalance in which the average energy expenditure of an individual is lower than his or her energy intake (i.e. calories from food intake). The energy homeostasis system in the human body tends to create an energy equilibrium (i.e. energy in =energy out) in the body to control body weight. However, psychological, pathological and social factors can force an energy imbalance, thereby generating body-weight fluctuations that depend on the long term ratio of food intake (FIN) and the total energy expenditure (TEE) of the individual. The physiological control of both energy expenditure and energy intake is highly dependent on the neuronal activity in the hypothalamus of the brain. The hypothalamus monitors various molecules (e.g. leptin, insulin and glucose) to determine the energy availability and accordingly, to modify the energy expenditure. Experimental data have shown that the energy expenditure can be artificially modulated by stimulating the hypothalamus, in particular the hypothalamic area called the ventromedial hypothalamic nucleus (VMH). Energy expenditure can be increased or decreased depending on the stimulating factors. Also, depending on the stimulating parameters, an increase in energy expenditure can trigger, among other things, a fat breakdown (lipolysis) which in turn leads to a reduction in appetite. In such a case, the body weight is reduced by the cumulative effects of both the increase in energy expenditure and the reduction of appetite.

The methods described herein may be used to identify, for example, the dorsomedial portion of the VMH or the Pe region. Once the brain structure (e.g., the dmVMH or the Pe) is identified, the target structure (e.g., the dmVMH or the Pe) may be modulated (inhibited or excited) or the activity of the fiber tracts directly or indirectly leading thereto may be modulated (inhibited or excited) to treat obesity, such as by DBS. In one embodiment using DTI MRI, the stria terminalis which connects the VMH to the amygdala is targeted at various locations along its path, for example, at the corticomedial amygdala, as it arches around the thalamus, just before it enters the VMH or at the VMH where it enters.

Other example treatments for obesity are addressed in, for example, U.S. Patent Publication No. 2008/0046012, to Covalin et al., which is incorporated by reference herein in its entirety.

XI. Treatment of Cachexia

In one embodiment, the nMEE is decreased and the food intake is increased via inhibition of the melanocortin system using high frequency DBS in the VMH, in particular in the medial portion of the VMH (mVHM) including the dorsomedial region of the VMH (dmVMH). In another embodiment, the nMEE is decreased and the food intake is increased via inhibition of the melanocortin system using very high frequency DBS in the VMH, in particular in the medial portion of the VMH (mVHM) including the dorsomedial region of the VMH (dmVMH). In another embodiment, feeding behavior is promoted by one or more frequencies administered at the LHA. In various embodiments, extremely low, very low, or low frequency excitatory stimulation can be administered to the LHA. In another embodiment, the nMEE is decreased and the food intake is increased via inhibition of the melanocortin using high frequency DBS in the VMH, in particular in the medial portion of the VMH (mVHM) including the dorsomedial region of the VMH (dmVMH), and feeding behavior is further promoted via low frequency stimulation of the LHA. In another embodiment, the nMEE is decreased and the food intake is increased via inhibition of the melanocortin using very high frequency DBS in the VMH, in particular in the medial portion of the VMH (mVHM) including the dorsomedial region of the VMH (dmVMH), and feeding behavior is further promoted via low frequency stimulation of the LHA and/or the Pe. In another embodiment, feeding behavior is promoted via medium range frequency stimulation of the PVN, in particular in the medial portion of the PVN. Food intake can also be increased by modulation of the NPY system via very low frequency stimulation, low frequency stimulation, or medium frequency stimulation of the DMH. Food intake can also be increased by modulation of the NPY system via low frequency stimulation of the DMH.

The methods described herein may be used to identify, for example, the dorsomedial portion of the VMH. Once the brain structure (e.g. the dmVMH) is identified, the target structure (e.g. the dmVMH) may be modulated (inhibited or excited) or the activity of the fiber tracts directly or indirectly related thereto may be modulated (inhibited or excited) to treat cachexia, such as by DBS.

XII. Treatment of Depression, Obsessive Compulsive Disorder (OCD) or Addiction

Empirical observations showed that the subgenual area, also called brodmann area 25 (BA25), is over active in many clinically depressed patients (Mayberg et al., 2005). BA25 is part of the cingulate region in the cerebral cortex. In humans, it is a strip in the caudal portion of the subcallosal area adjacent to the paraterminal gyrus. Areas such as the brainstem, hypothalamus and insula, which are associated with behaviors that are altered in clinically depressed people, are connected to BA25. Among those behaviors are sleep, appetite, libido, and neuroendocrine regulation. In addition, autonomic processes affecting motivation/reward and memory/learning mechanisms, which are impacted in depression, are modulated by the multiple neural pathways linking BA25 to orbitofrontal, medial prefrontal, and parts of the anterior and posterior cingulate cortices (Mayberg et al., 2005).

The methods described herein may be used to identify, for example, the subgenual area. Once this area is identified, it may be modulated (inhibited or excited) or the activity of the fiber tracts directly or indirectly related thereto may be modulated (inhibited or excited) to treat depression, such as by DBS.

The methods described herein may be used to identify, for example, the tracts that are near or project into/out of the nucleus accumbens to treat depression, obsessive compulsive disorder or addiction. Once this area is identified, it may be modulated (inhibited or excited) or the activity of the fiber tracts directly or indirectly related thereto may be modulated (inhibited or excited) in order to treat depression, obsessive compulsive disorder or addiction, such as by DBS. In one embodiment using DTI MRI, the medial forebrain bundle, which runs between the ventral tegmentum and the nucleus accumbens passing by the LHA, can be targeted at various locations along its path.

XIII. Treatment of Movement Disorders, Such as Parkinson's Disease

The STN is part of the brain stem and receives afferent connections from the primary motor area of the cerebral cortex, and the globus pallidus and in turn sends efferent back to the globus pallidus and the substantia nigra. The STN is part of a neural circuit which greatly influences motor control. In illnesses such as Parkinson's disease, a decrease in dopamine production in the Substantia Nigra generates a cascade of effects throughout the above-mentioned motor-control circuit leading to an overactive STN partially resulting in the characteristic tremor observed in Parkinson's patients.

The methods described herein may be used to identify, for example, the STN. Once the STN is identified, it may be modulated (inhibited or excited) or the activity of the fiber tracts directly or indirectly leading thereto may be modulated (inhibited or excited) to treat a movement disorder, such as Parkinson's Disease, such as by DBS. In some embodiments, electrical stimulation at frequencies ranging between 100 Hz and 150 Hz in the dorsolateral portion of the STN may result in the mitigation of Parkinson's symptoms. In other embodiments, higher frequencies may be used.

XIV. Kits

The present disclosure is also directed to kits that can be used to treat obesity in a patient. The kits can include a device, or component thereof, for performing DBS to a patient. In some embodiments, the kits can further include instructions for identifying a first brain structure by identifying the nerve tracts associated with the first brain structure or by identifying the nerve tracts associated with a brain region or second (or more) brain structure(s) and locating the first brain structure with reference to the brain region or other brain structure(s). In some embodiments, the kits can further include instructions for delivery of deep brain stimulation to a patient. The instructions can include methods described in more detail in the above description.

In various embodiments, the kits include a device or component thereof for treatment via DBS. The devices can include any commercial DBS system known. For example, one or more of the commercial IPGs (including, but not limited to IPGs described herein) may be included in the kit. In alternative embodiments, any leads and/or electrodes may be used separately, or in combination with the IPG to form the system. In certain embodiments, the IPG may be designed to generate frequencies greater than or equal to 1.0 kHz, 2.0 kHz, 3.0 kHz, 4.0 kHz, or 5.0 kHz. The instructions can include methods described in more detail in the above description.

The kits can further include instructions for targeting or identifying a brain structure. In various embodiments, the instructions provide directions to image a hypothalamic or other brain region using DTI MRI to identify a nerve tract, following the nerve tract to a first brain structure, and identifying the first brain structure based on the location and orientation of the nerve tract. The instructions can include methods described in more detail in the above detailed description.

The kits can further include instructions for treating obesity. In various embodiments, the instructions provide directions for implanting a device into a patient and treating a patient with obesity. The instructions can include any method disclosed herein for identifying a particular brain region or brain structure and then modulating the activity of a brain region or a brain structure by applying electrical stimulation to one or more brain regions or brain structures. The electrical stimulation can have any properties disclosed herein, including frequency, pulse width, amplitude, duration etc. The instructions can include methods described in more detail in the above description.

The kits can further include instructions for treating cachexia, depression, OCD, addiction or movement disorders by identifying a particular brain region or brain structure and then modulating the activity of a brain region or a brain structure by applying electrical stimulation to one or more brain regions or brain structures as described herein. The electrical stimulation can have any properties disclosed herein, including frequency, pulse width, amplitude, duration etc. The instructions can include methods described in more detail in the above description.

All references described herein are incorporated by reference in their entirety as if their contents were a part of the present disclosure.

EXAMPLES

The following examples are intended to be non-limiting and illustrative of aspects of the present disclosure.

Example 1

Modulation of the PVN may be used to treat obesity. The methods disclosed herein may be used to locate the target region during pre-surgical procedures and confirm during surgery that the electrode is in the target region or within range to modulate the target region with a low current, thereby reducing certain side effects A pre-surgical MRI image is taken, the patient is positioned in the MRI scanner and images are recorded applying diffusion gradients in several directions. Applying diffusion gradients in several directions allows for the identification of fiber tracts using DTI. The raw data may be processed by software such as MRI Studio ((https://www.mristudio.org/). Subsequent MRI images may be taken and images may be fused using other available software such as NeuroPlan™ (Integra Radionics, Burlington, Mass.). Images may be acquired at different facilities and at different times. Images are used to plan the surgery including the implantation route.

The PVN may be identified with reference to one or more nerve tracts. The nerve tracts include, but are not limited to, the hypothalamic-hypophyseal tract. The hypothalamic-hypophyseal tract runs from the PVN to the posterior lobe of the pituitary gland. Based on the DTI, the nerve tracts may be followed or otherwise used as a reference to identify the location of the PVN. Once the PVN is identified, its coordinates are recorded using the best available reference. The reference may be chosen using a stereotactic frame.

In order to modulate neuronal activity, an electrode is surgically implanted into the PVN using the coordinates obtained in the steps described above. An electrode may also be implanted at a point or points along the nerve tracts directly or indirectly related to the PVN to modulate the activity of the target structure. In another experiment, a different technique, such as a non-invasive technique, may be used to modulate the neuronal activity. All or part of the surgical procedure may be implemented under local anesthesia.

Example 2

Modulation of the dmVMH may be used to treat obesity or cachexia. The methods disclosed herein may be used to locate the target region during pre-surgical procedures and confirm during surgery that the electrode is in the target region or within range to modulate the target region with a low current, thereby reducing certain side effects.

A pre-surgical MRI image is taken, the patient is positioned in the MRI scanner and images are recorded applying diffusion gradients in several directions. Applying diffusion gradients in several directions allows for the identification of fiber tracts using DTI. The raw data may be processed by software such as MRI Studio ((https://www.mristudio.org/). Subsequent MRI images may be taken and images may be fused using other available software such as NeuroPlan™ (Integra Radionics, Burlington, Mass.). Images may be acquired at different facilities and at different times. Images are used to plan the surgery including the implantation route.

The dmVMH may be identified with reference to one or more nerve tracts. The nerve tracts include, but are not limited to, the stria terminalis and the dorsal longitudinal fasciculus nerve tracts. A branch of the stria terminalis carries fibers from the VMH to the amygdala located dorsally from the VMH and arching around the thalamus. The dorsal longitudinal fasciculus originates in the hypothalamic nuclei located medially around the third ventricle and then travels posteriorly before turning ventrally. The location of the dmVMH may be determined by identifying the medial origin of the dorsal longitudinal fasciculus and the dorsal path of the stria terminalis that originates at the VMH. In some embodiments, identifying the stria terminalis may be sufficient to successfully determine the location of the dmVMH. Based on the DTI, the nerve tracts may be followed or otherwise used as a reference to identify the location of the dmVMH. Once the dmVMH is identified, its coordinates are recorded using the best available reference. The reference may be chosen using a stereotactic frame.

In order to modulate neuronal activity, an electrode is surgically implanted into the dmVMH using the coordinates obtained in the steps described above. An electrode may also be implanted at a point or points along the nerve tract, such as the stria terminalis, directly or indirectly related to the dmVMH to modulate the activity of the target structure. In another experiment, a different technique, such as a non-invasive technique, may be used to modulate the neuronal activity. An increase in energy expenditure (EE) is expected and depending on stimulation parameters an increase in lipolysis can be expected, when stimulating the dorsomedial portion of the VMH. Therefore, in order to fine tune the location and/or identification of the brain structure, e.g., verify that the modulation is being applied to the desired targeted brain structure, at least one of the following is monitored: a) the oxygen consumption (VO2), b) the energy expenditure (EE), c) the carbon dioxide production (VCO2), and d) the respiratory quotient (RQ=VCO2/VO2). In some experiments, EE, VO2, VCO2, and RQ is monitored using indirect calorimetry. Using indirect calorimetry, an increase in lipolysis is signaled by a decrease in the RQ.

All or part of the surgical procedure may be implemented under local anesthesia.

Example 3

Modulation of the dmVMH may be used to treat obesity or cachexia. The methods disclosed herein may be used to locate the target region during pre-surgical procedures and confirm during surgery that the electrode is in the target region or within range to modulate the target region with a low current, thereby reducing certain side effects.

A pre-surgical MRI image is taken, the patient is positioned in the MRI scanner and images are recorded applying diffusion gradients in several directions. Applying diffusion gradients in several directions allows for the identification of fiber tracts using DTI. The raw data may be processed by software such as MRI Studio ((https://www.mristudio.org/). Subsequent MRI images may be taken and images may be fused using other available software such as NeuroPlan™ (Integra Radionics, Burlington, Mass.). Images may be acquired at different facilities and at different times. Images are used to plan the surgery including the implantation route.

The dmVMH may be identified with reference to one or more nerve tracts. The nerve tracts include, but are not limited to, the fornix and the mammillothalamic tract may be used to determine the location of the dmVMH. The fornix, projecting from the hippocampi to the mammillary bodies, travels through the hypothalamus and marks a separation between the medial and the lateral hypothalamus. The mammillothalamic tract projects from the mammillary bodies to the anterior nuclei of the dorsal thalamus. The relative location of the fornix and the mammilothalamic tract can be used as a reference to identify and target the dmVMH.

Based on the DTI, the nerve tracts may be followed or otherwise used as a reference to identify the location of the dmVMH. Once the dmVMH is identified, its coordinates are recorded using the best available reference. The reference may be chosen using a stereotactic frame.

In order to modulate neuronal activity, an electrode is surgically implanted into the dmVMH using the coordinates obtained in the steps described above. An electrode may also be implanted at a point or points along the nerve tracts directly or indirectly related to the dmVMH to modulate the activity of the target structure. In another experiment, a different technique, such as a non-invasive technique, may be used to modulate the neuronal activity. An increase in energy expenditure (EE) is expected and depending on stimulation parameters an increase in lipolysis can be expected, when stimulating the dorsomedial portion of the VMH. Therefore, in order to fine tune the location and/or identification of the brain structure, e.g., verify that the modulation is being applied to the desired targeted brain structure, at least one of the following is monitored: a) the oxygen consumption (VO2), b) the energy expenditure (EE), c) the carbon dioxide production (VCO2), and d) the respiratory quotient (RQ=VCO2/VO2). In some experiments, EE, VO2, VCO2, and RQ is monitored using indirect calorimetry. Using indirect calorimetry, an increase in lipolysis is signaled by a decrease in the RQ. All or part of the surgical procedure may be implemented under local anesthesia.

Example 4

Modulation of the LHA or nerve tracts directly or indirectly related to the LHA, such as the medial forebrain bundle, may be used to treat obesity, cachexia, depression, OCD or addiction. The methods disclosed herein may be used to locate the target region during pre-surgical procedures and confirm during surgery that the electrode is in the target region or within range to modulate the target region with a low or very low current, thereby reducing certain side effects.

A pre-surgical MRI image is taken, the patient is positioned in the MRI scanner and images are recorded applying diffusion gradients in several directions. Applying diffusion gradients in several directions allows for the identification of fiber tracts using DTI. The raw data may be processed by software such as MRI Studio ((https://www.mristudio.org/). Subsequent MRI images may be taken and images may be fused using other available software such as NeuroPlan™ (Integra Radionics, Burlington, Mass.). Images may be acquired at different facilities and at different times. Images are used to plan the surgery including the implantation route.

The LHA may be identified with reference to one or more nerve tracts. The nerve tracts include, but are not limited to, the ventral amygdalofungal pathway, the medial forebrain bundle, the dorsal longitudinal bundle and the fornix. In some embodiments, the ventral amygdalofungal pathway, the medial forebrain bundle, the dorsal longitudinal bundle and the fornix are used to identify the LHA. The LHA is flanked or traversed laterally by the medial forebrain bundle and the dorsal longitudinal bundle is located dorso-medially with respect to the LHA. The ventral amygdalofungal pathway goes into the LHA. The fornix can be considered as the boundary between the medial and lateral hypothalamus. The medial forebrain bundle also runs between the ventral tegmentum and the nucleus accumbens, passing by the LHA.

Based on the DTI, the nerve tracts may be followed or otherwise used as a reference to identify the location of the LHA. Once the LHA is identified, its coordinates are recorded using the best available reference. The reference may be chosen using a stereotactic frame.

In order to modulate neuronal activity, an electrode is surgically implanted into the LHA using the coordinates obtained in the steps described above. An electrode may also be implanted at a point or points along the nerve tracts directly or indirectly related to the LHA to modulate the activity of the target structure. In another experiment, a different technique, such as a non-invasive technique, may be used to modulate the neuronal activity. All or part of the surgical procedure may be implemented under local anesthesia.

Example 5

Modulation of the Pe may be used to treat obesity or cachexia. The methods disclosed herein may be used to locate the target region during pre-surgical procedures and confirm during surgery that the electrode is in the target region or within range to modulate the target region with a low current, thereby reducing certain side effects.

A pre-surgical MRI image is taken, the patient is positioned in the MRI scanner and images are recorded applying diffusion gradients in several directions. Applying diffusion gradients in several directions allows for the identification of fiber tracts using DTI. The raw data may be processed by software such as MRI Studio ((https://www.mristudio.org/). Subsequent MRI images may be taken and images may be fused using other available software such as NeuroPlan™ (Integra Radionics, Burlington, Mass.). Images may be acquired at different facilities and at different times. Images are used to plan the surgery including the implantation route.

The Pe may be identified with reference to one or more nerve tracts. The nerve tracts include, but are not limited to, the fornix and the amygdalofungal pathway. The fornix, projecting from the hippocampi to the mammillary bodies, travels through the hypothalamus separating the medial and the lateral hypothalamus. The ventral amygdalofungal pathway projecting from the amygdala has two main paths, one to the lateral hypothalamic area and a second one to the dorsomedial nucleus of the thalamus. The desired target area is in the LHA in close proximity to the fornix. The target can be located by identifying the fornix and then selecting the anterior-posterior position by the relative position of the ventral amygdalofungal pathway.

Based on the DTI, the nerve tracts may be followed or otherwise used as a reference to identify the location of the Pe. Once the Pe is identified, its coordinates are recorded using the best available reference. The reference may be chosen using a stereotactic frame.

In order to modulate neuronal activity, an electrode is surgically implanted into the Pe using the coordinates obtained in the steps described above. An electrode may also be implanted at a point or points along the nerve tracts directly or indirectly related to the Pe to modulate the activity of the target structure. In another experiment, a different technique, such as a non-invasive technique, may be used to modulate the neuronal activity. All or part of the surgical procedure may be implemented under local anesthesia.

Example 6

Modulation of the subgenual area (BA25) may be used to treat depression. The methods disclosed herein may be used to locate the target region during pre-surgical procedures and confirm during surgery that the electrode is in the target region or within range to modulate the target region with an appropriate current, thereby reducing certain side effects.

A pre-surgical MRI image is taken, the patient is positioned in the MRI scanner and images are recorded applying diffusion gradients in several directions. Applying diffusion gradients in several directions allows for the identification of fiber tracts using DTI. The raw data may be processed by software such as MRI Studio (https://www.mristudio.org/). Subsequent MRI images may be taken and images may be fused using other available software such as NeuroPlan™ (Integra Radionics, Burlington, Mass.). Images may be acquired at different facilities and at different times. Images are used to plan the surgery including the implantation route.

The subgenual area, also called brodmann area 25 (BA25), may be identified with reference to one or more nerve tracts. The nerve tracts may include the Cingulate Gyrus fibers. The Cingulate Gyrus fibers arc passing adjacent to the subgenual area as they traverse frontal fibers nearby. The target area can be identified by locating the Cingulate Gyrus fibers and following the fibers until the area where they pass adjacent to the subgenual area. The relative location of the fibers can be used as a reference to target the subgenual area.

Based on the DTI, the nerve tracts (cingulate gyrus fibers) may be followed or otherwise used as a reference to identify the location of the subgenual area. Once the subgenual area is identified, its coordinates are recorded using the best available reference. The reference may be chosen using a stereotactic frame.

In order to modulate neuronal activity to treat depression, an electrode is surgically implanted into the subgenual area using the coordinates obtained in the steps described above. An electrode may also be implanted at a point or points along the nerve tracts directly or indirectly related to the subgenual area to modulate the activity of the target structure. In another experiment, a different technique, such as a non-invasive technique, may be used to modulate the neuronal activity. Therefore, in order to fine tune the location and/or identification of the brain structure, e.g., verify that the modulation is being applied to the desired targeted brain structure, the patient, who is only under local anesthesia, may be asked to assess their mood, which may be affected immediately upon stimulation. All or part of the surgical procedure may be implemented under local anesthesia.

Example 7

Modulation of the subthalamic nucleus (STN) may be used to treat movement disorders, such as Parkinson's disease. The methods disclosed herein may be used to locate the target region during pre-surgical procedures and confirm during surgery that the electrode is in the target region or within range to modulate the target region with an appropriate current, thereby reducing certain side effects.

A pre-surgical MRI image is taken, the patient is positioned in the MRI scanner and images are recorded applying diffusion gradients in several directions. Applying diffusion gradients in several directions allows for the identification of fiber tracts using DTI. The raw data may be processed by software such as MRI Studio ((https://www.mristudio.org/). Subsequent MRI images may be taken and images may be fused using other available software such as NeuroPlan™ (Integra Radionics, Burlington, Mass.). Images may be acquired at different facilities and at different times. Images are used to plan the surgery including the implantation route.

The STN, and in particular its dorsolateral portion, may be identified with reference to one or more nerve tracts. The nerve tracts may include the ansa lenticularis (AL), the lenticular fasciculus (LF), subthalamic-occipitoparietal fibers, frontal fibers traversing the internal capsule, and the dentorubrothalamic fascicle. The AL pathway lays rostral to the NTS and the LF limits the NTS dorsally; passing above the NTS in a latero-medial trajectory. The subthalamic-occipitoparietal fibers intersect the dorsal portion of the STN. In one embodiment, the LF and the subthalamic-occipitoparietal fibers can be used to delimit the dorsolateral aspect of the STN. The target area can be identified by locating one or more of the nerve tracts and following the tracts into the STN or to a location near the STN. The relative location of the nerve tracts can be used as a reference to target the STN.

Based on the DTI, the nerve tracts may be followed or otherwise used as a reference to identify the location of the STN. Once the STN is identified, its coordinates are recorded using the best available reference. The reference may be chosen using a stereotactic frame.

In order to modulate neuronal activity to treat movement disorders, an electrode is surgically implanted into the STN using the coordinates obtained in the steps described above. An electrode may also be implanted at a point or points along the nerve tracts directly or indirectly related to the STN to modulate the activity of the target structure. In another experiment, a different technique, such as a non-invasive technique, may be used to modulate the neuronal activity. Therefore, in order to fine tune the location and/or identification of the brain structure, e.g., verify that the modulation is being applied to the desired targeted brain structure, the patients tremor intensity is observed, and the desired location is where the tremor is minimized with no adverse side effects. All or part of the surgical procedure may be implemented under local anesthesia.

Example 8

Modulation of the nucleus accumbens may be used to treat depression, OCD and/or addiction. The methods disclosed herein may be used to locate the target area during pre-surgical procedures and confirm during surgery that the electrode is in the target area or within range to modulate the target area with an appropriate current, thereby reducing certain side effects.

A pre-surgical MRI image is taken, the patient is positioned in the MRI scanner and images are recorded applying diffusion gradients in several directions. Applying diffusion gradients in several directions allows for the identification of fiber tracts using DTI. The raw data may be processed by software such as MRI Studio ((https://www.mristudio.org/). Subsequent MRI images may be taken and images may be fused using other available software such as NeuroPlan™ (Integra Radionics, Burlington, Mass.). Images may be acquired at different facilities and at different times. Images are used to plan the surgery including the implantation route.

The nucleus accumbens may be identified with reference to one or more nerve tracts. The target area can be identified by locating the one or more of the fibers disclosed herein and following the fibers until the area where they pass adjacent to or into the nucleus accumbens. The relative location of the fibers can be used as a reference to target the nucleus accumbens.

Based on the DTI, the nerve tracts may be followed or otherwise used as a reference to identify the location of the nucleus accumbens. Once the nucleus accumbens is identified, its coordinates are recorded using the best available reference. The reference may be chosen using a stereotactic frame.

In order to modulate neuronal activity to treat depression, OCD and/or addiction, an electrode is surgically implanted into the nucleus accumbens using the coordinates obtained in the steps described above. An electrode may also be implanted at a point or points along the nerve tracts directly or indirectly related to the nucleus accumbens to modulate the activity of the target area. In another experiment, a different technique, such as a non-invasive technique, may be used to modulate the neuronal activity. Therefore, in order to fine tune the location and/or identification of the brain structure, e.g., verify that the modulation is being applied to the desired targeted brain structure, the patient, who is only under local anesthesia, may be asked to assess their mood, which may be affected immediately upon stimulation. All or part of the surgical procedure may be implemented under local anesthesia.

Although the present disclosure has been described with reference to preferred embodiments, persons skilled in the art will recognize that changes may be made in form and detail without departing from the spirit and scope of the disclosure.

What is claimed is:

1. A method of identifying the ventromedial hypothalamic nucleus in a patient, the method comprising:
    imaging a brain region using Diffusion Tensor Imaging MRI to identify a nerve tract of a stria terminalis;
    obtaining additional images of the stria terminalis with Diffusion Tensor Imaging MRI to follow the nerve tract to the ventromedial hypothalamic nucleus;
    establishing a set of 3D coordinates for the stria terminalis and the ventromedial hypothalamic nucleus;
    implanting an electrode at the ventromedial hypothalamic nucleus or along the stria terminalis using the 3D coordinates;
    applying electrical deep brain stimulation via the electrode;
    monitoring oxygen consumption after implanting the electrode; and
    altering the location of the electrode based on the monitoring of oxygen consumption.

2. The method of claim 1, wherein the electrode is implanted at a location where the stria terminalis enters the ventromedial hypothalamic nucleus.

3. The method of claim 1, wherein the electrode is located on a cannula.

* * * * *